(12) United States Patent
Findeisen et al.

(10) Patent No.: US 7,662,595 B2
(45) Date of Patent: Feb. 16, 2010

(54) COMPOUNDS AND METHODS FOR ASSESSMENT OF MICROSATELLITE INSTABILITY (MSI) STATUS

(75) Inventors: Peter Findeisen, Schriesheim (DE); Sabine Merx, St. Leon-Rot (DE); Matthias Kloor, Ludwigshafen (DE); Magnus Von Knebel Doeberitz, Heidelberg (DE)

(73) Assignee: MTM Laboratories, AG, Heidelberg (DE)

( * ) Notice: Subject to any disclaimer, the term of this patent is extended or adjusted under 35 U.S.C. 154(b) by 33 days.

(21) Appl. No.: 11/576,597

(22) PCT Filed: Oct. 19, 2005

(86) PCT No.: PCT/EP2005/055375
§ 371 (c)(1),
(2), (4) Date: May 17, 2007

(87) PCT Pub. No.: WO2006/042854
PCT Pub. Date: Apr. 27, 2006

(65) Prior Publication Data
US 2008/0096197 A1    Apr. 24, 2008

(30) Foreign Application Priority Data
Oct. 19, 2004   (EP) .................................. 04105159

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......................... 435/91.2; 435/6; 536/23.1; 536/24.3; 536/24.33

(58) Field of Classification Search ........................ None
See application file for complete search history.

(56) References Cited

FOREIGN PATENT DOCUMENTS

| EP | 0 640 828 | 3/1995 |
|---|---|---|
| EP | 1 340 819 | 9/2003 |
| WO | WO 01/29262 | 4/2001 |
| WO | WO 02/10449 | 2/2002 |

OTHER PUBLICATIONS

Lucentini, J. 'Gene Association Studies Typically Wrong' The Scientist (Dec 20, 2004), p. 20.*
Juppner H. Bone (Aug 1995) vol. 17, No. 2, Supplement, pp. 39S-42S.*
Hegele R.A. Arterioscler Thromb Vasc Biol (2002) vol. 22, pp. 1058-1061.*
Siah S.P. et al. Breast Cancer Research and Treatment (2000) vol. 60, p. 135-142.*
Planck M. et al. Cancer Genetics and Cytogenetics (2002) vol. 134, p. 46-54.*
Banerjea A et al: "Colorectal cancers with mononucleotide microsatellite instability can be identified using microfabricated chip technology", Analytical Biochemistry, Academic Press, San Diego, CA, US, vol. 322, No. 1, Nov. 1, 2003, pp. 130-133, XP004458931.
Thorstensen L et al: "WNT1 inducible signaling pathway protein 3, WISP-3, a novel target gene in colorectal carcinomas with microsatellite instability", Gastroenterology, vol. 121, No. 6, Dec. 2001, pp. 1275-1280, XP002337304.
Sutter C et al: "Molecular screening of potential HNPCC patients using a multiplex microsatellite PCR system", Molecular and Cellular Probes, Academic Press, London, GB, vol. 13, No. 2, Apr. 1999, pp. 157-165, XP004450201.
Logette Emmanuelle et al: "The human caspase-2 gene: Alternative promoters, pre-mRNA splicing and AUG usage direct isoform-specific expression", Oncogene, vol. 22, No. 6, Feb. 13, 2003, pp. 935-946, XP002337305.
Database Geneseq [Online], Jul. 15, 2002, "Human spliced transcript detection oligonucleotide SEQ ID No: 8521", XP002337351, EBI accession No. GSN: ABN35773.
"ABI PRISM 310 Genetic Analyser—The measure of enabling technology", Product Bulletin, [Online] 2002, pp. 1-6, XP002337306, http://docs.appliedbiosystems.com/pebiodocs/00105575.pdf.>
"ABI PRISM 3100 Genetic analyser", Product Brochure from Applied Biosystems, [Online] 2001, pp. 1-8, XP002337307, http://docs.appliedbiosystems.com/pebiodocs/00103320.pdf>.
Database Geneseq [Online], Jul. 2, 2002, "Human gene specific PCR primer #866", XP002337352, EBI accession no. GSN: ABK66778.
Database Geneseq [Online], Jul. 26, 2002, "Human caspase2 antisense inhibitor oligonucleotide #36", XP002337353, EBI accession No. GSN: ABN74858.
Database Geneseq [Online], Nov. 20, 2003, "Human MDZ7 scanning oligonucleotide SEQ ID 5326", XP002337354, EBI accession No. GSN: ADB04340.
Database Genbank [Online], Dec. 17, 2003, "*Homo sapiens* caspase2, apoptosis-related cysteine protease (neural precursor cell expressed, developmentally down-regulated 2) (CASP2), transcript variant 1, mRNA", XP002373466, NCBI accession No. NM_032982.2.
Database Genbank [Online], Oct. 5, 2003, "*Homo sapiens* caspase2, apoptosis-related cysteine protease (neural precursor cell expressed, developmentally down-regulated 2) (CASP2), transcript variant 1, mRNA", XP002337350, NCBI accession No. NM_032982.1.

(Continued)

*Primary Examiner*—Stephen Kapushoc
(74) *Attorney, Agent, or Firm*—Howrey LLP; Viola T. Kung

(57) ABSTRACT

The present invention provides a method for assessment of the Microsatellite Instability (MSI) status of medically relevant conditions associated with MSI phenotype such as e.g. neoplastic lesions. The method is based on the analysis of a monomorphic T25 (CAT25) mononucleotide repeat located in the 3'-UTR of the Caspase 2 (CASP2) gene. Based on the determination of the length of the named mononucleotide repeat the presence or absence of MSI may be assessed. Determination of the length is performed in a single PCR procedure. Alternatively an enhanced assessment could be performed by combining the CAT25 marker with further markers such as BAT25 and BAT26 in a single multiplex PCR process.

11 Claims, 15 Drawing Sheets

OTHER PUBLICATIONS

Banerjea Ayan et al: "Colorectal cancers with microsatellite instability display mRNA expression signatures characteristic of increased immunogenicity", Molecular Cancer [Electronic resource], vol. 3, No. 1, Aug. 6, 2004, pp. 21(1)-21(11), XP002337308.

Takeuchi Seisho et al: "Frameshift mutations in caspase-5 and other target genes in leukemia and lymphoma cell lines having microsatellite instability", Leukemia Research, vol. 27, No. 4, Apr. 2003, pp. 359-361, XP002337320.

Findeisen Peter et al: "T-25 repeat in the 3'untranslated region of the CASP2 gene: A sensitive and specific marker for microsatellite instability in colorectal cancer", Cancer Research, vol. 65, No. 18, Sep. 2005, pp. 8072-8078, XP002373166.

International Search Report for PCT/EP2005/055375, mailed Apr. 18, 2006.

International Preliminary Report on Patentability for PCT/EP2005/055375, issued Apr. 24, 2007.

* cited by examiner

| case | Reference Panel (ICG HNPCC) | | | | | |
|---|---|---|---|---|---|---|
| | BAT25 | BAT26 | D17S250 | D2S123 | D5S346 | CAT25 |
| HD-01 | ● | ● | ● | ○ | ● | ● |
| HD-02 | ● | ● | ● | ○ | ● | ● |
| HD-03 | ● | ● | ● | ● | ● | ● |
| HD-04 | ● | ● | ● | ● | ○ | ● |
| HD-05 | ● | ● | ● | ● | ○ | ● |
| HD-06 | ● | ● | ● | ○ | ○ | ● |
| HD-07 | ● | ● | ○ | ● | ○ | ● |
| HD-08 | ● | ● | ● | ● | ● | ● |
| HD-09 | ● | ● | ● | ○ | ● | ● |
| HD-10 | ● | ● | ● | ○ | ● | ● |
| HD-11 | ● | ● | ● | ● | ● | ● |
| HD-12 | ● | ● | ● | ● | ● | ● |
| HD-13 | ● | ● | ○ | ○ | ○ | ● |
| HD-14 | ● | ● | n. a. | ● | ● | ● |
| HD-15 | ● | ○ | ● | ● | ● | ● |
| HD-16 | ● | ● | ● | ● | ● | ● |
| HD-17 | ● | ● | ● | ● | ● | ● |
| HD-18 | ● | ● | ○ | ● | ● | ● |
| HD-19 | ● | ● | ○ | ● | ● | ● |
| HD-20 | ● | ● | ● | ● | ● | ● |
| HD-21 | ● | ● | ● | ● | ● | ● |
| HD-22 | ● | ● | ● | ● | ● | ● |
| HD-23 | ● | ● | ● | ● | ○ | ● |
| HD-24 | ● | ● | ○ | ● | ○ | ● |
| HD-25 | ● | ● | ● | ● | ● | ● |
| HD-26 | ● | ● | ● | ● | ● | ● |
| HD-27 | ● | ● | ● | ● | ● | ● |
| HD-28 | ● | ● | ● | ● | ● | ● |
| HD-29 | ● | ● | ● | ● | ○ | ● |
| HD-30 | ● | ● | ● | ● | ● | ● |
| HD-31 | ● | ● | ○ | ● | ● | ● |
| HD-32 | ○ | ● | ● | ● | ● | ● |
| HD-33 | ● | ● | ● | ● | ○ | ● |
| HD-34 | ● | ● | ○ | ○ | ○ | ● |
| HD-35 | ● | ● | ○ | ○ | ○ | ● |
| HD-36 | ● | ● | ● | ● | ● | ● |
| HD-37 | ● | ● | ● | ● | ● | ● |
| HD-38 | ● | ● | ● | ● | ● | ● |
| HD-39 | ● | ● | ● | ○ | ● | ● |
| HD-40 | ● | ● | ● | ● | ● | ● |
| HD-41 | ● | ● | ● | ● | ● | ● |
| HD-42 | ● | ● | ● | ● | ● | ● |
| HD-43 | ● | ● | ● | ● | ● | ● |
| HD-44 | ● | ● | ● | ● | ● | ● |
| HD-45 | ● | ● | ○ | ● | ● | ● |
| HD-46 | ● | ● | ● | ● | ● | ● |
| HD-47 | ● | ● | ○ | ○ | ○ | ● |
| HD-48 | ● | ● | ● | ● | ○ | ● |
| HD-49 | ● | ● | ● | ● | ● | ● |
| HD-50 | ● | ● | ● | ● | ● | ● |
| HD-51 | ● | ● | ● | ● | ● | ● |
| HD-52 | ● | ● | ● | ● | ● | ● |
| HD-53 | ● | ● | ● | ● | ● | ● |
| HD-54 | ● | ● | ● | ● | ● | ● |
| HD-55 | ● | ● | ● | ● | ● | ● |
| HD-56 | ● | ● | ● | ● | ● | ● |
| HD-57 | ● | ● | ● | ● | ● | ● |
| MSI pos. | 56 | 56 | 46 | 46 | 45 | 57 |
| total | 57 | 57 | 56 | 57 | 57 | 57 |
| sensitivity (%) | 98.2 | 98.2 | 82.1 | 80.7 | 78.9 | 100.0 |

Figure 1

BAT25

| Size (bp) | Caucasian (n=117) | | African (n=102) | | Asian (n=79) | |
|---|---|---|---|---|---|---|
| 112 | 0 | | 1 (1.0%) | | 0 | |
| 113 | 0 | | 0 | | 0 | |
| 114 | 0 | 0% | 1 (1.0%) | | 0 | |
| 115 | 0 | | 7 (6.9%) | 26.5% | 0 | 0% |
| 116 | 0 | | 8 (7.8%) | | 0 | |
| 117 | 0 | | 2 (2.0%) | | 0 | |
| 118 | 0 | | 2 (2.0%) | | 0 | |
| 119 | 0 | | 6 (5.9%) | | 0 | |
| 120 | 17 (14.5%) | | 22 (21.6%) | | 4 (5.1%) | |
| 121 | 78 (66.7%) | 100% | 37 (36.3%) | 73.5% | 43 (54.4%) | 100% |
| 122 | 22 (18.8%) | | 16 (15.7%) | | 32 (40.5%) | |

BAT26

| Size (bp) | Caucasian (n=117) | | African (n=102) | | Asian (n=79) | |
|---|---|---|---|---|---|---|
| 104 | 0 | | 1 (1.0%) | | 0 | |
| 105 | 0 | | 0 | | 0 | |
| 106 | 0 | | 5 (4.9%) | | 0 | |
| 107 | 0 | | 11 (10.8%) | | 0 | |
| 108 | 0 | | 0 | | 0 | |
| 109 | 0 | 0.9% | 1 (1.0%) | 21.6% | 0 | 2.5% |
| 110 | 0 | | 1 (1.0%) | | 0 | |
| 111 | 0 | | 0 | | 0 | |
| 112 | 0 | | 0 | | 0 | |
| 113 | 0 | | 0 | | 0 | |
| 114 | 0 | | 0 | | 1 (1.3%) | |
| 115 | 1 (0.9%) | | 3 (2.9%) | | 1 (1.3%) | |
| 116 | 28 (23.9%) | | 20 (19.6%) | | 13 (16.5%) | |
| 117 | 64 (54.7%) | 99.1% | 36 (35.3%) | 77.5% | 61 (77.2%) | 97.5% |
| 118 | 24 (20.5%) | | 23 (22.5%) | | 3 (3.8%) | |
| 119 | 0 | | 1 (1.0%) | 1.0% | 0 | |

CAT25

| Size (bp) | Caucasian (n=200) | | African (n=102) | | Asian (n=79) | |
|---|---|---|---|---|---|---|
| <146 | 0 | | 0 | | 0 | |
| 146 | 18 (9.0%) | | 4 (3.9%) | | 2 (2.5%) | |
| 147 | 128 (64.0%) | 100% | 34 (33.3%) | 100% | 35 (44.3%) | 100% |
| 148 | 54 (27.0%) | | 64 (62.7%) | | 42 (53.2%) | |
| >148 | 0 | | 0 | | 0 | |

Figure 2

| case | Mono27 | NR-21 | NR-22 | NR-24 | CAT25 |
|---|---|---|---|---|---|
| HD-01 | 9 | 10 | 8 | 8 | 9 |
| HD-02 | na | 4 | 3 | 7 | 6 |
| HD-04 | 7 | 7 | 6 | 5 | 9 |
| HD-05 | 11 | 6 | 3 | 6 | 7 |
| HD-06 | 9 | 4 | 5 | 2 | 7 |
| HD-07 | 16 | 13 | 9 | 9 | 9 |
| HD-08 | 12 | 9 | 5 | 5 | 6 |
| HD-09 | 10 | 8 | 4 | na | 11 |
| HD-10 | 6 | 7 | 1 | 1 | 4 |
| HD-11 | 10 | 6 | 4 | 7 | 8 |
| HD-12 | 9 | 10 | 7 | 4 | 13 |
| HD-13 | 5 | 6 | 4 | 4 | 8 |
| HD-15 | 2 | 2 | 0 | na | 2 |
| HD-16 | 5 | 10 | 4 | 5 | 10 |
| HD-18 | 10 | 6 | 4 | 5 | 7 |
| HD-19 | 11 | 10 | 3 | 8 | 9 |
| HD-20 | 7 | 9 | 5 | 5 | 5 |
| HD-21 | 9 | 8 | na | 5 | 7 |
| HD-23 | 8 | 9 | 4 | na | 8 |
| HD-24 | 7 | 11 | 5 | na | 10 |
| HD-25 | 9 | 9 | 7 | 6 | 10 |
| HD-26 | 4 | 7 | 4 | 2 | 7 |
| HD-31 | 7 | 8 | 7 | 7 | 13 |
| HD-32 | 5 | 4 | 2 | 3 | 2 |
| HD-33 | 7 | 9 | 8 | na | 9 |
| HD-34 | 10 | 6 | 1 | 8 | 9 |
| HD-36 | 10 | 8 | 8 | 11 | 8 |
| HD-39 | na | 2 | 3 | 6 | 2 |
| HD-41 | na | 9 | 6 | 8 | 12 |
| HD-44 | 13 | 8 | 6 | 8 | 11 |
| HD-46 | 8 | 5 | 4 | na | 11 |
| HD-47 | 10 | 4 | 4 | 5 | 8 |
| HD-49 | 10 | 7 | 6 | 6 | 8 |
| HD-53 | 3 | 4 | na | 2 | 5 |
| HD-54 | 5 | 7 | 6 | 4 | 11 |
| HD-56 | 7 | 7 | 5 | 3 | 9 |
| HD-57 | 10 | 6 | 8 | 7 | 11 |
| MSI | 34 | 37 | 34 | 31 | 37 |
| total | 34 | 37 | 35 | 31 | 37 |
| sensitivity (%) | 100 | 100 | 97,1 | 100 | 100 |
| without normal tissue (%) | 100 | 100 | 97,1 | 96,8 | 100 |

Figure 6

| Marker | Accession No. | Repeat Type | Lengths (bp) | Primer | | Commercial Applications | |
|---|---|---|---|---|---|---|---|
| CD4 | M86525 | (AAAAG)n | 134-179 | fwd1 | CCAGGAAGTTGAGGCTGCAGTGAA | unknown | |
| | | | | rev1 | TTGGAGTCGCAAGCTGAACTAGCG | | |
| | | | 86-141 | fwd2 | GCCTGAGTGACAGAGTGAGAACC | | |
| | | | | rev2 | TTGGAGTCGCAAGCTGAACTAGC | | |
| D3S1358 | 11449919 | (ATAG)n | 99-147 | fwd | ACT GCA GTC CAA TCT GGG T | | |
| | | | | rev | ATG AAA TCA ACA GAG GCT TG | | |
| | | | | | | AmpFISTR® Profiler Plus™ | GenePrint® PowerPlex™ 2.1 |
| D5S818 | G08446 | (AGAT)n | 133-169 | fwd | GGGTGATTTTCCTCTTTGGT | | |
| | | | | rev | TGATTCCAATCATAGCCACA | | |
| | | | | | | AmpFISTR® Profiler Plus™ | GenePrint® PowerPlex™ 1.1 |
| CSF1PO | X14720 | (AGAT)n | 291-331 | fwd | AACCTGAGTCTGCCAAGGACTAGC | | |
| | | | | rev | TTCCACACACCACTGGCCATCTTC | | |
| | | | | | | AmpFISTR® Profiler Plus™ | GenePrint® PowerPlex™ 1.1 |
| D7S820 | G08616 | (GATA)n | 194-234 | fwd | TGTCATAGTTTAGAACGAACTAACG | | |
| | | | | rev | CTGAGGTATCAAAAACTCAGAGG | | |
| | | | | | | AmpFISTR® Profiler Plus™ | GenePrint® PowerPlex™ 1.1 |
| D8S1179 | AF216671 | (TATC)n | 157-205 | fwd | TTTTTGTATTTCATGTGTACATTCG | | |
| | | | | rev | CGTAGCTATAATTAGTTCATTTTCA | | |
| | | | | | | AmpFISTR® Profiler Plus™ | GenePrint® PowerPlex™ 2.1 |
| D12S391 | G08921 | (AGAT)n(AGAC)m(AGAT)n | 209-253 | fwd | AACAGGATCAAATGGATGCAT | unknown | |
| | | | | rev | TGGCTTTTAGACCTGGACTG | | |
| D13S317 | G09017 | (GATA)n | 157-201 | fwd | ACAGAAGTCTGGGATGTGGA | | |
| | | | | rev | GCCCAAAAAGACAGACAGAA | | |
| | | | | | | AmpFISTR® Profiler Plus™ | GenePrint® PowerPlex™ 1.1 |

Figure 10

| Locus | Accession | Repeat | Size range | Primers | Kit 1 | Kit 2 |
|---|---|---|---|---|---|---|
| D16S593 | G07925 | | 141-173 | fwd GATCCCAAGCTCTTCCTCTT | | |
| | | | | rev ACGTTTGTGTGTGCATCTGT | AmpFlSTR® Profiler Plus™ | GenePrint® PowerPlex™ 1.1 |
| D18S51 | X91254 | (GATA)n | 262-342 | fwd CAA ACC CGA CTA CCA GCA AC | | |
| | | | | rev GAG CCA TGT TCA TGC CAC TG | AmpFlSTR® Profiler Plus™ | GenePrint® PowerPlex™ 2.1 |
| D21S11 | M84567 | (TCTA)n(TCTG)m | 202-260 | fwd GTG AGT CAA TTC CCC AAG | | |
| | | | | rev GTT GTA TTA GTC AAT GTT CTC C | AmpFlSTR® Profiler Plus™ | GenePrint® PowerPlex™ 2.1 |
| F13A1 | M21986 | (AAAG)n | 179-235 | fwd1 GAGGTTGCACTCCAGCCTTT | | |
| | | | | rev1 ATGCCATGCAGATTAGAAA | | unknown |
| | | | 279-335 | fwd2 GAGGTTGCACTCGAGCCTTTGCAA | | |
| | | | | rev2 TTCCTGAATCATCCCAGAGCCACA | | |
| F13B | M64554 | (AAAT)n | 169-193 | fwd TGAGGTGGTGTACTACCATA | | |
| | | | | rev GATCATGCCATTGCACTCTA | | unknown |
| HPRTB | M26434 | (AGAT)n | 259-303 | fwd ATGCCACAGATAATACACATCCCC | | |
| | | | | rev CTCTCCAGAATAGTTAGATGTAGG | | |
| FIBRA | M64982 | TTTC (complex) | 158-314 | fwd GCCCCATAGGTTTTGAACTCA | | |
| | | | | rev TGATTTGTCTGTAATTGCCAGC | AmpFlSTR® Profiler Plus™ | GenePrint® PowerPlex™ 2.1 |
| VWA | M25858 | (AGAT)n | 122-182 | fwd CCCTAGTGGATAAGAATAATC | | |
| | | | | rev GGACAGATGATAAATACATAGGATGGATGG | AmpFlSTR® Profiler Plus™ | GenePrint® PowerPlex™ 1.1 |
| LPL | D83550 | (AAAT)n | 105-133 | fwd1 CTGACCAAGGATAGTGGGATATAG | | |
| | | | | rev1 GGTAACTGAGCGAGACTGTGTCT | | |
| | | | 111-139 | fwd2 ATCTGACCAAGGATAGTGGGATATA | | |
| | | | | rev2 CCTGGGTAACTGAGCGAGACTGTGTC | | |
| HUMTH01 | D00269 | (AATG)n | 171-215 | fwd1 GTGGGCTGAAAAGCTCGGGCTCTGG | | |
| | | | | rev1 ATTCAAAGGGTATCTGGGCTCTGG | | |
| | | | 146-190 | fwd2 GTGGGCTGAAAAGCTCCCGATTAT | | |
| | | | | rev2 GTGATTCCCATTGGCCTGTTCCTC | AmpFlSTR® Profiler Plus™ | GenePrint® PowerPlex™ 1.1/2.1 |

Figure 10
continued

| | | | |
|---|---|---|---|
| Penta D | AC001752 | (AAAGA)n | 376-409 | Promega Power Plex 16 |
| Penta E | AC027004 | (AAAGA)n | 379-474 | Promega Power Plex 16 |

Additional polymorphic markers suitable for testing sample identity can be found at http://www.cstl.nist.gov/biotech/strbase/

1fwd 5'-CTGCCTCAAAGGGACTGC-3'
1rev 5'-CCTTCCCGATCCTTGATAAGT-3'   corresponding to an amplification product length of 144 bp 2fwd 5'-CCTAGAAACCTTTATCCCTGCTT-3'
2rev 5'-GAGCTTGCAGTGAGCTGAGA-3'   corresponding to an amplification product length of 148 bp 3fwd 5'- AACCTTTATCCCTGCTTATCTGA-3'
3rev 5'- AGTTGGAGCTTGCAGTGAGC-3'   corresponding to a predicted amplification product length of 148 bp 4fwd 5'-CCTAGAAACCTTTATCCCTGCTT-3'
4rev 5'-GAGCTTGCAGTGAGCTGAGA-3'   corresponding to a predicted amplification product length of 149 bp 5fwd 5'-ACTTCCCAACTTCCCTGTTCTT-3'
5rev 5'-AGAATGGCGTGAACCCGGGA-3'   corresponding to a predicted amplification product length of 144 bp 6fwd 5'-GAAACTTCCCAACTTCCCTGT-3'
6rev 5'-GGCGTGAACCCGGGAGTTGG-3'   corresponding to a predicted amplification product length of 142 bp 7fwd 5'-AAACTTCCCAACTTCCCTGTTC-3'
7rev 5'-ATCATGAGGTCAGGAGATCA-3' corresponding to a predicted amplification product length of 278 bp 8fwd 5'-AACTTCCCAACTTCCCTGTTC-3'
8rev 5'-ATCATGAGGTCAGGAGATC-3'   corresponding to a predicted amplification product length of 277 bp 9fwd 5'-CTTCCCAACTTCCCTGTTCTT-3'
9rev 5'-GGATCATGAGGTCAGGAGA-3' corresponding to a predicted amplification product length of 277 bp 10fwd 5'-ACCTAGAAACCTTTATCCCTGCT T-3'
10rev 5'-CATGAGGTCAGGAGATCAA-3' corresponding to a predicted amplification product length of 305 bp 11fwd 5'-CCTAGAAACCTTTATCCCTGCT-3'
11rev 5'-TTTGGGAGGCTGAGGTGGGT-3'   corresponding to a predicted amplification product length of 328 bp 12fwd 5'-AACCTAGAAACCTTTATCCCTGCT-3'
12rev 5'-ACTTTGGGAGGCTGAGGTGGG-3' corresponding to a predicted amplification product length of 332 bp

SEQUENCE LISTING

```
<160> NUMBER OF SEQ ID NOS: 96

<210> SEQ ID NO 1
<211> LENGTH: 18
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(18)

<400> SEQUENCE: 1
ctgcctcaaa gggactgc                                                    18

<210> SEQ ID NO 2
<211> LENGTH: 21
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
```

<222> LOCATION: (1)..(21)

<400> SEQUENCE: 2
ccttcccgat ccttgataag t                                             21

<210> SEQ ID NO 3
<211> LENGTH: 23
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(23)

<400> SEQUENCE: 3
cctagaaacc tttatccctg ctt                                           23

<210> SEQ ID NO 4
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 4
gagcttgcag tgagctgaga                                               20

<210> SEQ ID NO 5
<211> LENGTH: 23
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(23)

<400> SEQUENCE: 5
aacctttatc cctgcttatc tga                                           23

<210> SEQ ID NO 6
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 6
agttggagct tgcagtgagc                                               20

<210> SEQ ID NO 7
<211> LENGTH: 22
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(22)

<400> SEQUENCE: 7
acttcccaac ttccctgttc tt                                              22

<210> SEQ ID NO 8
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 8
agaatggcgt gaacccggga                                                 20

<210> SEQ ID NO 9
<211> LENGTH: 21
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 9
gaaacttccc aacttccctg t                                               21

<210> SEQ ID NO 10
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 10
ggcgtgaacc cgggagttgg                                                 20

<210> SEQ ID NO 11
<211> LENGTH: 22
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(22)

<400> SEQUENCE: 11
aaacttccca acttccctgt tc                                              22

<210> SEQ ID NO 12
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 12
atcatgaggt caggagatca                                                 20

<210> SEQ ID NO 13

-continued

```
<211> LENGTH: 21
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 13
aacttcccaa cttccctgtt c                                              21

<210> SEQ ID NO 14
<211> LENGTH: 19
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(19)

<400> SEQUENCE: 14
atcatgaggt caggagatc                                                 19

<210> SEQ ID NO 15
<211> LENGTH: 21
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 15
cttcccaact tccctgttct t                                              21

<210> SEQ ID NO 16
<211> LENGTH: 19
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(19)

<400> SEQUENCE: 16
ggatcatgag gtcaggaga                                                 19

<210> SEQ ID NO 17
<211> LENGTH: 24
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 17
acctagaaac ctttatccct gctt                                           24

<210> SEQ ID NO 18
<211> LENGTH: 19
<212> TYPE: DNA
<213> ORGANISM: Artificial Sequence
<220> FEATURE:
```

<223> OTHER INFORMATION: Description of the artificial sequence: Primer
<220> FEATURE:
<221> NAME/KEY: misc_feature
<222> LOCATION: (1)..(19)

<400> SEQUENCE: 18
catgaggtca ggagatcaa                                                    19

<210> SEQ ID NO 19
<211> LENGTH: 22
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(22)

<400> SEQUENCE: 19
cctagaaacc tttatccctg ct                                                22

<210> SEQ ID NO 20
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 20
tttgggaggc tgaggtgggt                                                   20

<210> SEQ ID NO 21
<211> LENGTH: 24
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 21
aacctagaaa cctttatccc tgct                                              24

<210> SEQ ID NO 22
<211> LENGTH: 21
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 22
actttgggag gctgaggtgg g                                                 21

<210> SEQ ID NO 23
<211> LENGTH: 21
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 23
attaacttcc tacaccacaa c                                               21

<210> SEQ ID NO 24
<211> LENGTH: 19
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(19)

<400> SEQUENCE: 24
gtagagcaag accaccttg                                                  19

<210> SEQ ID NO 25
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 25
aaacaggatg cctgccttta                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 26
ggactttcca cctatgggac                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 27
ggaagaatca aatagacaat                                                 20

<210> SEQ ID NO 28
<211> LENGTH: 24
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 28
gctggccata tatatattta aacc                                            24

<210> SEQ ID NO 29
<211> LENGTH: 21
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 29
actcactcta gtgataaatc g                                         21

<210> SEQ ID NO 30
<211> LENGTH: 25
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(25)

<400> SEQUENCE: 30
agcagataag acagtattac tagtt                                     25

<210> SEQ ID NO 31
<211> LENGTH: 21
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 31
cccttccttg ctgtcactac a                                         21

<210> SEQ ID NO 32
<211> LENGTH: 18
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(18)

<400> SEQUENCE: 32
tgaacccagg aggcagag                                             18

<210> SEQ ID NO 33
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 33
gtcgcagcac taaaaatgga                                           20

<210> SEQ ID NO 34
<211> LENGTH: 20

```
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 34
gaagggcatt caagcacact                                                    20

<210> SEQ ID NO 35
<211> LENGTH: 22
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(22)

<400> SEQUENCE: 35
aatttagcaa accctagcct tg                                                 22

<210> SEQ ID NO 36
<211> LENGTH: 22
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(22)

<400> SEQUENCE: 36
aagagctact tcaaagcaag ca                                                 22

<210> SEQ ID NO 37
<211> LENGTH: 20
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 37
agcagtggca gctcagaaat                                                    20

<210> SEQ ID NO 38
<211> LENGTH: 19
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(19)

<400> SEQUENCE: 38
gcctcttgat cacgtccaa                                                     19

<210> SEQ ID NO 39
<211> LENGTH: 23
<212> TYPE: DNA
<213> ORGANISM: Artificial Sequence
<220> FEATURE:
<223> OTHER INFORMATION: Description of the artificial sequence: Primer
```

```
<220> FEATURE:
<221> NAME/KEY: misc_feature
<222> LOCATION: (1)..(23)

<400> SEQUENCE: 39
tttgttatat cccattaggt gcc                                              23

<210> SEQ ID NO 40
<211> LENGTH: 21
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 40
agcctggtga cagagtgaga c                                                21

<210> SEQ ID NO 41
<211> LENGTH: 23
<212> TYPE: DNA
<213> ORGANISM: Artificial Sequence
<220> FEATURE:
<223> OTHER INFORMATION: Description of the artificial sequence: Primer
<220> FEATURE:
<221> NAME/KEY: misc_feature
<222> LOCATION: (1)..(23)

<400> SEQUENCE: 41
tatggctcta aaatgctctg ttc                                              23

<210> SEQ ID NO 42
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 42
taaatgtatg tctcccctgg                                                  20

<210> SEQ ID NO 43
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 43
attcctactc cgcattcaca                                                  20

<210> SEQ ID NO 44
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)
```

```
<400> SEQUENCE: 44
gaggcttgtc aaggacataa                                                    20

<210> SEQ ID NO 45
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 45
aattcggatg ccatccagtt                                                    20

<210> SEQ ID NO 46
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 46
ccattgctga attttacctc                                                    20

<210> SEQ ID NO 47
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 47
attgtgccat tgcattccaa                                                    20

<210> SEQ ID NO 48
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 48
ttgcagtgag ctgagattgc                                                    20

<210> SEQ ID NO 49
<211> LENGTH: 21
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 49
ggtggatcaa atttcacttg g                                                  21
```

```
<210> SEQ ID NO 50
<211> LENGTH: 19
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(19)

<400> SEQUENCE: 50
actgcagtcc aatctgggt                                              19

<210> SEQ ID NO 51
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 51
atgaaatcaa cagaggcttg                                             20

<210> SEQ ID NO 52
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 52
ccaggaagtt gaggctgcag tgaa                                        24

<210> SEQ ID NO 53
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 53
ttggagtcgc aagctgaact agcg                                        24

<210> SEQ ID NO 54
<211> LENGTH: 23
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(23)

<400> SEQUENCE: 54
gcctgagtga cagagtgaga acc                                         23

<210> SEQ ID NO 55
<211> LENGTH: 23
<212> TYPE: DNA
```

```
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(23)

<400> SEQUENCE: 55
ttggagtcgc aagctgaact agc                                              23

<210> SEQ ID NO 56
<211> LENGTH: 19
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(19)

<400> SEQUENCE: 56
actgcagtcc aatctgggt                                                   19

<210> SEQ ID NO 57
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 57
atgaaatcaa cagaggcttg                                                  20

<210> SEQ ID NO 58
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 58
gggtgatttt cctctttggt                                                  20

<210> SEQ ID NO 59
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 59
tgattccaat catagccaca                                                  20

<210> SEQ ID NO 60
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
```

<221> NAME/KEY: misc_feature
<222> LOCATION: (1)..(24)

<400> SEQUENCE: 60
aacctgagtc tgccaaggac tagc                                                24

<210> SEQ ID NO 61
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 61
ttccacacac cactggccat cttc                                                24

<210> SEQ ID NO 62
<211> LENGTH: 25
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(25)

<400> SEQUENCE: 62
tgtcatagtt tagaacgaac taacg                                               25

<210> SEQ ID NO 63
<211> LENGTH: 23
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(23)

<400> SEQUENCE: 63
ctgaggtatc aaaaactcag agg                                                 23

<210> SEQ ID NO 64
<211> LENGTH: 25
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(25)

<400> SEQUENCE: 64
tttttgtatt tcatgtgtac attcg                                               25

<210> SEQ ID NO 65
<211> LENGTH: 25
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(25)

<400> SEQUENCE: 65

-continued

```
cgtagctata attagttcat tttca                                          25

<210> SEQ ID NO 66
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 66
aacaggatca atggatgcat                                                20

<210> SEQ ID NO 67
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 67
tggcttttag acctggactg                                                20

<210> SEQ ID NO 68
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 68
acagaagtct gggatgtgga                                                20

<210> SEQ ID NO 69
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 69
gcccaaaaag acagacagaa                                                20

<210> SEQ ID NO 70
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 70
gatcccaagc tcttcctctt                                                20
```

```
<210> SEQ ID NO 71
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 71
acgtttgtgt gtgcatctgt                                                   20

<210> SEQ ID NO 72
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 72
caaacccgac taccagcaac                                                   20

<210> SEQ ID NO 73
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 73
gagccatgtt catgccactg                                                   20

<210> SEQ ID NO 74
<211> LENGTH: 18
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(18)

<400> SEQUENCE: 74
gtgagtcaat tccccaag                                                     18

<210> SEQ ID NO 75
<211> LENGTH: 22
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(22)

<400> SEQUENCE: 75
gttgtattag tcaatgttct cc                                                22

<210> SEQ ID NO 76
<211> LENGTH: 20
<212> TYPE: DNA
<213> ORGANISM: Artificial sequence
```

```
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 76
gaggttgcac tccagccttt                                                    20

<210> SEQ ID NO 77
<211> LENGTH: 19
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(19)

<400> SEQUENCE: 77
atgccatgca gattagaaa                                                     19

<210> SEQ ID NO 78
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 78
gaggttgcac tcgagccttt gcaa                                               24

<210> SEQ ID NO 79
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 79
ttcctgaatc atcccagagc caca                                               24

<210> SEQ ID NO 80
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(20)

<400> SEQUENCE: 80
tgaggtggtg tactaccata                                                    20

<210> SEQ ID NO 81
<211> LENGTH: 20
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
```

<222> LOCATION: (1)..(20)

<400> SEQUENCE: 81
gatcatgcca ttgcactcta                                               20

<210> SEQ ID NO 82
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 82
atgccacaga taatacacat cccc                                          24

<210> SEQ ID NO 83
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 83
ctctccagaa tagttagatg tagg                                          24

<210> SEQ ID NO 84
<211> LENGTH: 21
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 84
gccccatagg ttttgaactc a                                             21

<210> SEQ ID NO 85
<211> LENGTH: 22
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(22)

<400> SEQUENCE: 85
tgatttgtct gtaattgcca gc                                            22

<210> SEQ ID NO 86
<211> LENGTH: 21
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(21)

<400> SEQUENCE: 86

```
ccctagtgga taagaataat c                                              21

<210> SEQ ID NO 87
<211> LENGTH: 30
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(30)

<400> SEQUENCE: 87
ggacagatga taaatacata ggatggatgg                                     30

<210> SEQ ID NO 88
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 88
ctgaccaagg atagtgggat atag                                           24

<210> SEQ ID NO 89
<211> LENGTH: 23
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(23)

<400> SEQUENCE: 89
ggtaactgag cgagactgtg tct                                            23

<210> SEQ ID NO 90
<211> LENGTH: 25
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(25)

<400> SEQUENCE: 90
atctgaccaa ggatagtggg atata                                          25

<210> SEQ ID NO 91
<211> LENGTH: 26
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(26)

<400> SEQUENCE: 91
cctgggtaac tgagcgagac tgtgtc                                         26

<210> SEQ ID NO 92
```

```
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 92
gtgggctgaa aagctcccga ttat                                              24

<210> SEQ ID NO 93
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 93
attcaaaggg tatctgggct ctgg                                              24

<210> SEQ ID NO 94
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 94
gtgggctgaa aagctcccga ttat                                              24

<210> SEQ ID NO 95
<211> LENGTH: 24
<212> TYPE: DNA
<213> ORGANISM: Artificial sequence
<220> FEATURE:
<223> OTHER INFORMATION: Description of the artificial sequence: Primer
<220> FEATURE:
<221> NAME/KEY: misc_feature
<222> LOCATION: (1)..(24)

<400> SEQUENCE: 95
gtgattccca ttggcctgtt cctc                                              24

<210> SEQ ID NO 96
<211> LENGTH: 25
<212> TYPE: DNA
<213> ORGANISM: Artificial sequence
<220> FEATURE:
<223> OTHER INFORMATION: Description of the artificial sequence: Simple
      sequence repeats
<220> FEATURE:
<221> NAME/KEY: misc_feature
<222> LOCATION: (1)..(25)

<400> SEQUENCE: 96
tttttttttt tttttttttt ttttt                                             25
```

COMPOUNDS AND METHODS FOR ASSESSMENT OF MICROSATELLITE INSTABILITY (MSI) STATUS

This application is a National Stage of International Application PCT/EP2005/055375, filed Oct. 19, 2005, published Apr. 27, 2006, under PCT Article 21(2) in English; which claims the priority of EP 04105159.0, filed Oct. 19, 2004.

The present invention provides a method for assessment of the Microsatellite Instability (MSI) status of medically relevant conditions associated with MSI phenotype such as e.g. neoplastic lesions. The method is based on the analysis of a monomorphic mononucleotide repeat located in the 3'-UTR of the Caspase 2 (CASP2) gene. Based on the determination of the length of the named mononucleotide repeat the presence or absence of MSI may be assessed. Determination of the length is performed in a single PCR procedure. Alternatively an enhanced assessment could be performed by combining the CASP2 marker with further markers such as BAT25 and BAT26 in a single multiplex PCR process.

BACKGROUND OF THE INVENTION

A deficient DNA mismatch repair (MMR) system is observed in about 10-15% of all colorectal carcinomas and in up to 90% of hereditary non-polyposis colorectal cancer (HNPCC) patients. Tumors with MMR defects acquire mutations in short repetitive DNA stretches, a phenomenon termed microsatellite instability. The determination of microsatellite status in colon cancer is of increasing relevance, since (1) microsatellite status is an independent prognostic factor in colorectal cancer, (2) the efficacy of adjuvant chemotherapy seems to be dependent on microsatellite status of the tumor, and (3) microsatellite instability is the most important molecular screening tool for the identification of HNPCC patients and families affected by germline mutations in MMR genes. Therefore, routine MSI testing appears to be justified for all colorectal cancer cases.

Microsatellite instability is observed in about 10-15% of sporadic colorectal carcinomas (CRCS) and in up to 90% of hereditary non-polyposis colorectal cancer (HNPCC) patients that harbor germline mutations in DNA mismatch repair (MMR) genes (for a review see Lynch and de la Chapelle "Hereditary colorectal cancer", N Engl J Med. 2003 Mar. 6; 348(10):919-932). CRCs displaying the microsatellite instability (MSI) phenotype possess particular pathological and clinical features. MSI-H CRCs are often localized in the proximal colon and present with a dense intratumoral lymphocyte infiltration (Smyrk et al. "Tumor-infiltrating lymphocytes are a marker for microsatellite instability in colorectal carcinoma, Cancer 2001 Jun. 15; 91(12):2417-22; Dolcetti et al. "High prevalence of activated intraepithelial cytotoxic T lymphocytes and increased neoplastic cell apoptosis in colorectal carcinomas with microsatellite instability, Am J Pathol. 1999 June; 154(6):1805-13). Several studies report a better prognosis for MSI-H CRC patients (Gryfe et al. "Tumor microsatellite instability and clinical outcome in young patients with colorectal cancer", N Engl J Med. 2000 Jan. 13; 342(2):69-77; Wright et al. "Prognostic significance of extensive microsatellite instability in sporadic clinicopathological stage C colorectal cancer", Br J Surg. 2000 September; 87(9):1197-202); Samowitz et al. "Microsatellite instability in sporadic colon cancer is associated with an improved prognosis at the population level", Cancer Epidemiol Biomarkers Prev. 2001 September; 10(9):912-23). Interestingly, the susceptibility towards chemotherapy seems to be dependent on microsatellite status of colorectal tumor cells (Claij, "Microsatellite instability in human cancer: a prognostic marker for chemotherapy?", Exp Cell Res. 1999 Jan. 10; 246(1):1-10); Hemminki et al. "Microsatellite instability is a favorable prognostic indicator in patients with colorectal cancer receiving chemotherapy, Gastroenterology. 2000 October; 119(4):921-8; Watanabe et al. "A change in microsatellite instability caused by cisplatin-based chemotherapy of ovarian cancer", Br J Cancer 2001 Sep. 28; 85(7):1064-9). The DNA MMR system appears to be involved in apoptosis induction via DNA-damaging agents, in vitro, several cell lines with a defective mismatch repair system have been shown to be resistant to such agents (Claij "Microsatellite instability in human cancer: a prognostic marker for chemotherapy?", Exp Cell Res. 1999 Jan. 10; 246(1):1-10; Bawa and Xiao "A mutation in the MSH5 gene results in alkylation tolerance, Cancer Res. 1997 Jul. 1; 57(13):2715-20"; Carethers et al. "Mismatch repair proficiency and in vitro response to 5-fluorouracil, Gastroenterology 1999 July, 117(1):123-31"). In a study of Ribic et al. ("Tumor microsatellite-instability status as a predictor of benefit from fluorouracil-based adjuvant chemotherapy for colon cancer", N Engl J Med. 2003 Jul. 17; 349(3):247-57), a tendency towards a shorter overall survival was observed in 5-fluorouracil (5-FU) chemotherapy-treated patients with MSI-H CRC, whereas patients with MSS CRC benefited from adjuvant 5-FU therapy. In a different study, the improved survival of CRC patients treated with chemotherapy was restricted to MSS cases, whereas no effect was detected in the MSI-H group (Carethers et al. "Use of 5-fluorouracil and survival in patients with microsatellite-unstable colorectal cancer", Gastroenterology 2004 February; 126(2):688-9).

These data point to the clinical significance of microsatellite status in CRC and provide good reasons for routine MSI testing of all colorectal cancer cases. The current standard method however is time-consuming, laborious, and expensive.

At present, MSI-testing is usually only applied to patients preselected upon clinical criteria (Bethesda guidelines, Boland et al. "A National Cancer Institute Workshop on Microsatellite Instability for cancer detection and familial predisposition: development of international criteria for the determination of microsatellite instability in colorectal cancer", Cancer Res. 1998 Nov. 15; 58(22):5248-57), because the standard testing procedure recommended by the ICG-HNPCC workshop (Boland et al. "A National Cancer Institute Workshop on Microsatellite Instability for cancer detection and familial predisposition: development of international criteria for the determination of microsatellite instability in colorectal cancer", Cancer Res. 1998 Nov. 15; 58(22):5248-57),) implies a considerable laboratory workload: Five microsatellite markers including two mononucleotide repeats (BAT26 and BAT25) and three dinucleotide repeats (D2S123, D5S346, D17S250) have to be amplified from DNA of tumor and normal tissue. A panel of additional five MSI-markers is used for MSI classification of borderline cases. These numerous markers that require analysis of matched normal DNA of the same patient make MSI analysis a laborious and costly testing procedure that is not applicable for high throughput screening.

Therefore, a simplified testing strategy is required for high throughput testing. To reduce the workload of MSI testing, several techniques have been suggested in previous publications. Immunohistochemistry with monoclonal antibodies specific for MLH1 and MSH2 is commonly accepted as a useful tool to identify HNPCC-related tumors (Marcus et al. 1999 "Immunohistochemistry for hMLH1 and hMSH2: a practical test for DNA mismatch repair-deficient tumors, Am J Surg Pathol. 1999 October; 23(10):1248-55", Lindor et al. "Immunohistochemistry versus microsatellite instability testing in phenotyping colorectal tumors", J Clin Oncol. 2002 Feb. 15; 20(4):897-9; Umar et al. "Revised Bethesda Guidelines for hereditary nonpolyposis colorectal cancer (Lynch syndrome) and microsatellite instability", J Natl Cancer Inst. 2004 Feb. 18; 96 (4):261-8) and sensitivity can further be enhanced by the inclusion of additional antibodies recognizing MSH6 and PMS2. Compared to PCR-based MSI testing, IHC has some advantages, mainly the lower costs that were estimated to be less than one-third when compared to standard MSI analysis (Debniak et al. "Value of pedigree/clinical data, immunohistochemistry and microsatellite instability analyses in reducing the cost of determining hMLH1 and hMSH2 gene mutations in patients with colorectal cancer", Eur J. Cancer. 2000 January; 36(1):49-54).

However, there are several limitations of IHC as a screening method when used alone. Some cases of MSI-H tumors are missed (Lindor et al. Immunohistochemistry versus microsatellite instability testing in phenotyping colorectal tumors", J Clin Oncol. 2002 Feb. 15; 20(4):897-9), and false negative results have been reported due to intratumor heterogeneity, so staining of at least two independent samples for each carcinoma was recommended (Chapusot et al. "Microsatellite instability and intratumoural heterogeneity in 100 right-sided sporadic colon carcinomas", Br J Cancer 2002 Aug. 12; 87(4):400-4). Furthermore, staining artifacts may result from formalin fixation procedure, especially when large tissue blocks are used (reviewed by Werner et al. 2000). Hence, the use of PCR-based MSI detection methods is indispensable for correct MSI classification at present. To minimize costs of PCR-based MSI testing, the use of BAT26 alone has been suggested in several studies (Zhou et al. "Determination of the replication error phenotype in human tumors without the requirement for matching normal DNA by analysis of mononucleotide repeat microsatellites", Genes Chromosomes Cancer 1998 February; 21(2):101-7; Cravo et al. "BAT-26 identifies sporadic colorectal cancers with mutator phenotype: a correlative study with clinico-pathological features and mutations in mismatch repair genes", J. Pathol. 1999 July; 188(3):252-7; Stone et al. "Optimising methods for determining RER status in colorectal cancers", Cancer Lett. 2000 Feb. 28; 149(1-2):15-20), even without the need for matching normal tissue (Hoang et al. "BAT-26, an indicator of the replication error phenotype in colorectal cancers and cell lines", Cancer Res. 1997 Jan. 15; 57(2):300-3). Although this approach may be sufficient for the majority of MSI-H cases, it does not equal the sensitivity of the ICG-HNPCC standard panel since there are false negative results. Additionally, depending on the ethnic origin of the tested individuals, shortened BAT26 alleles which have been reported in up to 5.3% (most frequent in Afro-American people, Pyaft et al. "Polymorphic variation at the BAT-25 and BAT-26 loci in individuals of African origin. Implications for microsatellite instability testing", Am J. Pathol. 1999 August; 155(2):349-53) lead to false positive classification when corresponding normal tissue is not available (Perucho "Correspondence re: C. R. Boland et al., A National Cancer Institute workshop on microsatellite instability for cancer detection and familial predisposition: development of international criteria for the determination of microsatellite instability in colorectal cancer. Cancer Res., 58: 5248-5257, 1998.", Cancer Res. 1999 Jan. 1; 59(1):249-56). Similarly, for BAT25 alleles aberrant from the general "wild type" have been detected in 0.6% to 6.8% of cases (Ichikawa et al. "DNA variants of BAT-25 in Japanese, a locus frequently used for analysis of microsatellite instability", Jpn J Clin Oncol. 2001 July; 31 (7):346-8); Pyatt et al. "Polymorphic variation at the BAT-25 and BAT-26 loci in individuals of African origin. Implications for microsatellite instability testing", Am J Pathol. 1999 August; 155(2):349-53). Therefore, Suraweera et al. ("Evaluation of tumor microsatellite instability using five quasimonomorphic mononucleotide repeats and pentaplex PCR", Gastroenterology. 2002 December; 123(6):1804-11) recommended a pentaplex PCR system using BAT25, BAT26, and three additional mononucleotide markers that allowed reliable microsatellite typing in the majority of gastrointestinal tumors and cell lines that were tested. However, MSI status of a considerable number of tumors was pre-typed by only dinucleotide markers or BAT25/BAT26 alone, thus hampering the evaluation of the diagnostic sensitivity and specificity of the pentaplex system. Sutter et al. (Molecular screening of potential HNPCC patients using a multiplex microsatellite PCR system", Mol Cell Probes. 1999 April; 13(2):157-65) recommended a combination of five markers in a multiplex system that reached 100% sensitivity and specificity, but only when used in combination with corresponding normal tissue.

The currently recommended procedure using the standard ICG-HNPCC marker panel for this purpose is costly and time-consuming. It is therefore desirable to establish a new microsatellite testing procedure. This procedure could e.g. include a novel marker highly indicative for MSI that could simplify the current protocols for MSI evaluation.

The compounds and methods disclosed according to the present invention provide for improvement of the microsatellite testing procedure. The procedure disclosed herein is prone to simplify MSI analysis in colorectal cancer without reducing the diagnostic sensitivity or specificity. The inventors found that the 3'-UTR T25 mononucleotide repeat of the CASP2 gene (in the following referred to as CAT25) may be used for an efficient and sensitive determination of the microsatellite status in specimens. In certain embodiments the disclosed marker may also be combined with the established microsatellite markers BAT25 and BAT26 in one multiplex amplification reaction.

BRIEF DESCRIPTION OF THE INVENTION

In the search for more efficient screening strategies, inventors surprisingly identified a monomorphic T-25 repeat in the 3'-UTR of the CASP2 gene (CAT25) that may be used as a marker for MSI status. Based on this monomorphic marker molecule a method for assessment of MSI status of medically relevant conditions associated with MSI phenotype has been designed. The method comprises the steps of i) determination of the presence or absence of mutations in the T-25 repeat located in the 3'-UTR of the CASP2 gene; and ii) assessment of the MSI status based on the presence or absence of mutations, wherein the presence of mutations is indicative of the presence of MSI-H status.

BRIEF DESCRIPTION OF THE FIGURES

FIG. 1: Table summarizing results of mutational analysis for several microsatellite-loci in samples: The table shows the mutations of microsatellite markers in MSI-H CRC. Black circles in this figure indicate mutated microsatellites, open circles indicate wild type microsatellites, n.a. indicates, that sample was not analyzable. For details see Example 1.

FIG. 2: Table displaying the main product lengths of BAT25, BAT26 and CAT25: The main product lengths of BAT25, BAT26, and CAT25 observed in normal DNA samples from donors of different ethnic origin. Variant BAT25 and BAT26 alleles which might lead to misclassification of MSI were observed in 26.5% and 21.6%, respectively. CAT25 products ranged between 146 bp and 148 bp in all tested individuals (n=381). Gray boxes—range of product lengths observed in normal DNA from Caucasian individuals. For details see Example 1.

FIG. 6: Table summarizing the results of mutational analysis for combinations of CAT25 with previously published quasimonomorphic mononucleotide markers in samples: For the quasimonomorphic mononucleotide markers relative shift lengths observed in PCR amplification are given in the table for a panel of patient samples. Sensitivites for detection of MSI is calculated compared to the MSI result obtained with the standard Bethesda panel (total). For details see Example 4.

FIG. 10: List of exemplary polymorphic typing markers Exemplary primer sequences (SEQ ID NOs: 52-95) for the amplification of polymorphic typing markers which can be used in combination with CAT25 for the verification of sample identity.

FIG. 11: Primer Pairs for amplification of the CAT25 Sequences (SEQ ID NOs: 1-22) are given as examples for primer pairs for amplification of CAT25 repeat for a method according to the present invention. The primers displayed may e.g. be incorporated in a kit according to the present invention.

DETAILED DESCRIPTION OF THE INVENTION

Figure 3:
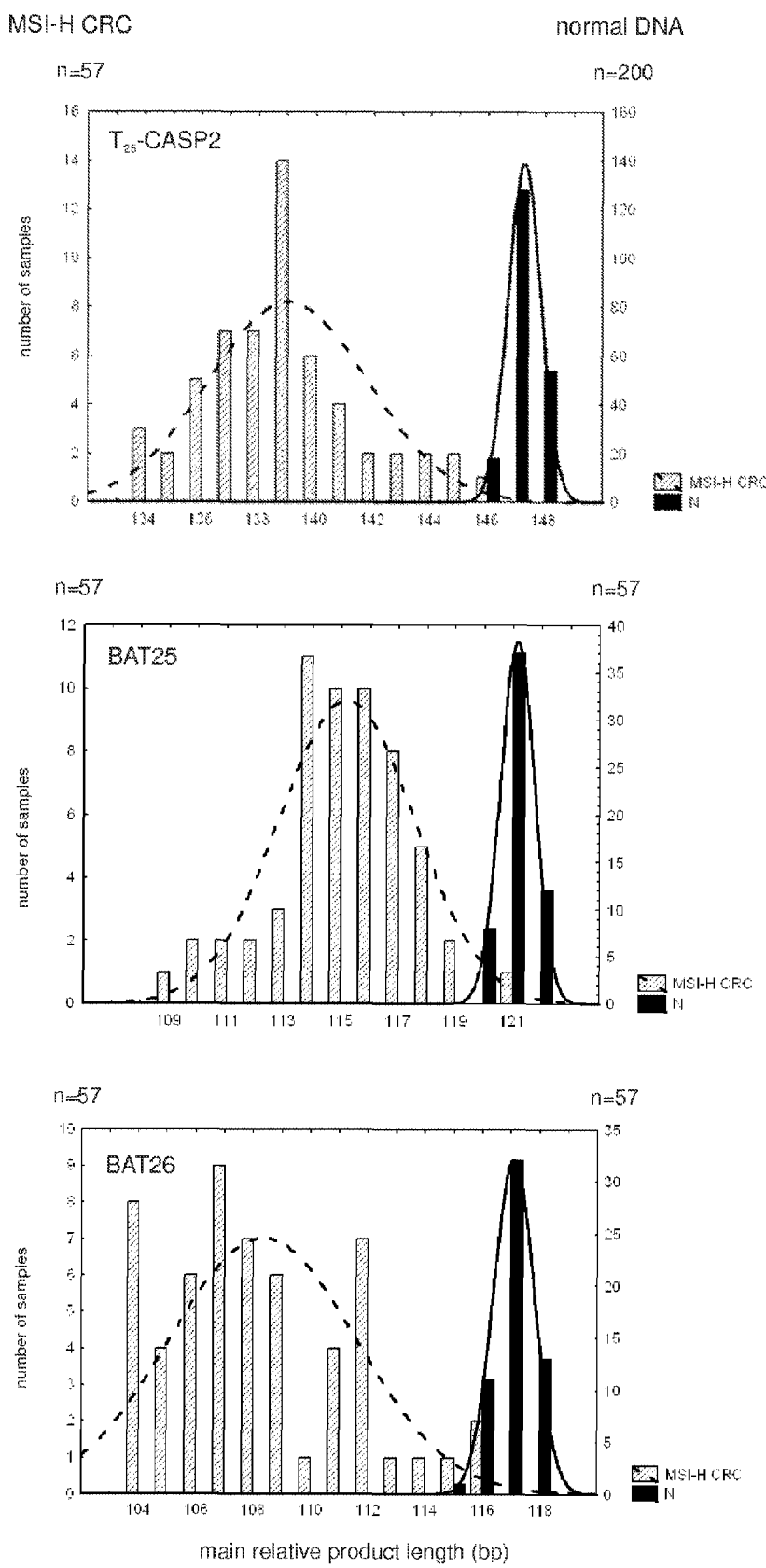
FIG. 3: Distribution of CASP2, BAT25, and BAT26 product lengths in colonic tumours: Relative product lengths observed in MSI-H CRCs (shaded columns) and non-tumorous DNA samples (black columns). About two-thirds of the tested normal DNA collective (mainly from Caucasian donors) presented with a main CASP2 product length of 147 bp. Because no variations exceeding one nucleotide were observed, the detection of MSI was possible in all but one case without the analysis of corresponding normal tissue. For details see Example 1.

One aspect of the present invention is a method for assessment of the MSI status of medically relevant conditions associated with MSI such as e.g. tumors. The method comprises determining the presence or absence of mutations in the T-25 repeat located in the 3'-UTR of the CASP2 gene. This may e.g. comprise the determination of the length of the nucleic acid of the 3'-UTR.

A second aspect of the present invention is a kit for performance of the method according to the present invention.

A third aspect of the present invention is the use of probes complementary or reverse complementary to the CASP2 gene for manufacture of a kit for assessment of the MSI status of medically relevant conditions associated with MSI.

A further aspect of the present invention is a system for the assessment of the MSI status of medically relevant conditions based on the detection of mutations in the T-25 repeat of the 3'-UTR of the CASP2 gene (CAT 25).

A fifth aspect of the present invention is a nucleic acid complementary or reverse complementary to CASP2 gene for determination of the MSI status of medically relevant conditions.

The present invention is based on the application of a marker molecule that is characterized by a high degree of mutation frequency in the MSI-H tumors of interest and no detectable mutations in MSS tissue specimens. The characteristics of this marker molecule enable for establishment of a highly sensitive and specific detection method of MSI-H cases on the basis of an easy mutation detection.

Casp2 or Caspase 2 gene as used in the context of the present invention in it's various grammatical forms refers to Caspase 2 also denominated as Apoptosis-Related Cysteine Protease located on chromosomal region 7q34-q35 (UniGene Cluster Hs.433103). Alternative splicing leads to the transcription of different isoforms of CASP2, the reference nucleic acid sequence of the longest cDNA isoform spanning the longest chromosomal region and consisting of eleven exons is identified by sequence accession No. NM_032982.2. The version of the sequence referenced to is available from December 2003 on at NCBI database and was subject to several updates since this date. Alternative isoforms identified by sequence accession Nos NM_032983, NM_032984, and NM_001224 all share a 3' exon identical to exon 11 of cDNA sequence NM_032982 that contains the T25 repeat described above. The protein encoded by this gene is also known in the art as ICH-1 protease and is identified as protein P42575 and classified as an enzyme belonging to the EC 3.4.22.-group of hydrolases (enzyme nomenclature database, SwissProt). The Casp2 protein is required for stress-related apoptosis induction by release of cytochrome c and Smac from mitochondria and by translocation of Bax from the cytoplasm to mitochondria (Lassus et al. 2002). Generally Casp2 gene as used herein refers to single as well as double stranded nucleid acids and therefore comprises the sequences as found on the coding strand of the Casp2 gene as well as sequences revers complementry thereto. Furthermore the Sequences of Casp2 gene as well as fragments thereof shall be understood under the term Casp2 gene or Casp2 nucleic acid.

Casp2 gene or Casp2 nucleic acid as used in the context of the present invention shall furthermore comprise the T-25 repeat located in the 3'-UTR of the CASP2 gene, according to the present invention referring to the T-25 repeat located at position nt 2685 to 2709 of the second version of NM_032982 sequence as available at NCBI database from December 2003 on. Casp2 gene or Casp2 nucleic acid as used in the context of the present invention therefore refers to the coding sequence, the 5' regulatory sequences and the 3' untranslated regions of the Casp2 gene. CAT25 as used herein shall especially refer to the T-25 repeat located in the 3'-UTR of the CASP2 gene, according to the present invention referring to the T-25 repeat located at position nt 2685 to 2709 as mentioned above.

This repeat has a length of 25 nucleotides according to the cited database entry. This T-25 repeat according to the present invention is regarded as monomorphic. In the context of the present invention the monomorphic T-25 repeat may also have a repeat length of T-24 and T-26. As used in the context of the present invention the term "T-25 repeat" or "CAT25" comprises also the T-24 and the T-26 forms.

The named T-25 repeat also called CAT25 located at position nt 2685 to 2709 of the NM_032982 sequence exhibits a relative fragment length of 148 nucleotides in an amplification system as disclosed herein in the Examples.

The T-25 repeat as disclosed herein is monomorphic as no relative allele lengths of below 146 nt or above 148 nt could be detected in samples originating from normal healthy individuals of different ethnic background (Caucasian, African, Asian). Relative allele length as used herein shall refer to an allele-specific fragment length generated in an nucleic acid amplification reaction. Therefore the term "monomorphic" as used in the context of the present invention refers to the uniform length of the presence T-25 repeat in samples from normal healthy individuals and includes a range of deviation of +/−one nucleotide. Alleles containing a T-24, a T-25 or a T-26 repeat are regarded as being monomorphic respective the T-25 repeat microsatellite.

The allele lengths of 146 nt and 148 nt respectively cited above are detected using a detection system as given in Example 1. It is known to those of skill in the art that due to technical issues, small variations of detected relative product lengths may occur. In certain embodiments of the present invention the variation of detected fragments lengths may be restricted to 1 bp or less by design of the detection system. Generally the detection system for application according to the present invention must ensure suitable sensitivity and/or specificity of the MSI analysis procedure. However, e.g. one reference sample could be included in each analysis. In this embodiment the reference sample could be used as external control and may consist of any CASP2 PCR product with a previously determined product length. In addition, various other methods for the detection of the mutations may be applied. The allele lengths detected in the respective detection system are dependent on the parameters of the system. Those of skill in the art know how the respective allele lengths have to be amended corresponding to amendments to the parameters of the detection system. Within the context of the present invention the allele lengths of 146 nt and 148 nt respectively that may be detected with the detection system as disclosed in the examples hereto shall be cited. However any allele length determined using another system but corresponding to the named allele lengths shall be comprised when using the cited allele lengths herein. Generally an allele length differing from the allele length given in accession number NM_032982 by +2 nt or −2 nt or more in the oligo-T repeat located in the 3'-UTR of the named sequence, shall be regarded as being indicative for the presence of a mutation.

The CASP2 T-25 (CAT25) repeat disclosed herein exhibits mutations in MSI-H cancers with high prevalence. No CAT25 alterations are present in control MSS colorectal carcinoma samples. The mean shift length in MSI-H CRCs as detected in a PCR based detection assay for CAT25 is comparable to those seen with BAT26 and BAT25. Finally, in normal healthy individual no alleles differing more than one nucleotide from the relative wild type length were observed for the CAT25 T-25 repeat in the CASP2 3'-UTR. Compared to the additional markers in the multiplex panel suggested by Suraweera (Suraweera et al., 2002), the CAT25 mononucleotide repeat displays a higher mutation frequency and a longer mean shift length.

In one embodiment of the present invention a combination of CAT25 with the two mononucleotides BAT25 and BAT26 from the standard ICG-HNPCC panel may be applied to improve diagnostic sensitivity and specificity.

Generally the marker molecule disclosed herein is applicable to all medically relevant conditions where an analysis of the MSI status is indicated for assessment of diagnosis or for stratification of individuals for adequate therapy. Those medically relevant conditions comprise e.g. tumors of various kind and nature.

It is known to those of skill in the art that the applicability of certain markers for MSI analysis can vary between different types of tumors (Lawes et al., 2003) as well as between different stages of one tumor type. It has recently been reported that BAT26 showed lower sensitivity in colorectal adenomas (Grady et al., 1998), ovarian cancer (Sood et al., 2001) and endometrial cancer with significantly reduced mean basepair deletions (Duval et al., 2002).

In the experiments leading to the present invention the inventors could show that CAT25 is a microsatellite marker of more universal application. It turned out that the T-25 repeat in the 3'-UTR of the CASP2 gene (CAT25) was indicative of MSI-H status in all tested tumor entities and mutations were absent in MSS tumors. In addition to MSI-H colorectal carcinomas, colorectal adenomas, endometrial carcinomas, ovarian cancers, and urothelial cancers presented with pronounced shifts at the CAT25 repeat (Examples 2 and 3). A broad applicability is therefore one feature of the microsatellite marker disclosed herein.

Furthermore it is known in the art that microsatellite markers are commonly useful in a group of individuals restricted to certain ethnic origin. The CAT25 marker in contrast proved to be applicable over a wide range of individuals of ethnically different origins. The broad applicability of the CAT25 therefore also pertains to applicability to different ethnic groups of individuals.

Nucleic acid molecules according to the present invention may comprise any kind of polynucleotides or fragments thereof. Polynucleotides may for example include single-stranded (sense or antisense) or double-stranded molecules, and may be DNA (genomic, cDNA or synthetic) or RNA. RNA molecules comprise as well hnRNA (containing introns) as mRNA (not containing introns). According to the present invention the polynucleotides may also be linked to any other molecules, such as support materials or detection marker molecules, and may, but need not, contain additional coding or non-coding sequences. The term nucleic acids as used in the present invention shall also comprise any kind of synthetic or modified nucleic acids such as synthetic polynucleotides or fragments thereof, peptide nucleic acids (PNAs) or the like. Specific types of such synthetic or modified nucleic acids are known to those of skill in the art. In certain embodiment synthetic nucleic acids may comprise uncommon or artificial nucleosides or analogues thereof.

In certain embodiments the nucleic acids according to the present invention are modified or altered nucleic acids. The alteration or modification may be performed for alteration of the necessary hybridization conditions or for introduction of labels or reporter molecules or for any other reason. Specific types of such synthetic or modified nucleic acids are known to those of skill in the art.

In certain embodiment synthetic nucleic acids may comprise uncommon or artificial nucleosides (e.g. with altered sugar components or with altered purine or pyrimidine components, etc.) or nucleotides (e.g. thiophosphate or phosphorothioate nucleotides) or analogues thereof. Such alterations may e.g. comprise the introduction of labels such as radioactive labels (e.g. as radiation emitting radioisotopes $^{32}P$, $^{35}S$, $^{14}C$, $^{3}H$, etc.), introduction of colored or fluorescent (e.g. maleimide, iodoacetamide, etc.) components or of binding moieties such as biotin or the like into the nucleic acids. In certain embodiments the introduction of thiol groups in the sugar and or the pyrimidine or purine (e.g. 4-thiouridine or the like) component may be of certain advantage for the subsequent detection reaction. Reactive forms of fluorescent dyes such as e.g. Oregon Green 488, Rhodamine Green, Rhodamine Red, Texas Red, fluorescein, tetramethylrhodamine, biotin, DSB biotin and DNP succinimidyl esters may be used for labeling of the nucleic acids applied in the methods according to the present invention. As the case may be the labels may be couples via spacers to the nucleic acids. Such spacers comprise e.g. aminohexanoyl spacers or the like. In certain embodiments of the present invention the nucleic acids are modified in a way to allow for FRET analysis of the hybridization reaction. the methods for the provision of modified and altered nucleic acids are known to those of ordinary skill in the art. The above examples of modifications, alterations and labels are for exemplification only and are not intended to restrict the scope of the invention. Various other modifications and labels for nucleic acids are known to those of skill in the art. In certain embodiments of the invention any of the methods known in the art may be applied to nucleic acids for use in a method according to the present invention.

The nucleic acids for application in a method according to the present invention are nucleic acids of a CASP2 gene as defined above. The nucleic acids according to the present invention may also be complementary or reverse complementary to any CASP2 nucleic acid. The nucleic acids for use in a method according to the present invention in this respect may deviate from the primary structure of the nucleic acid sequence as given in accession number NM_032982. These deviations or variations in the primary structure of the nucleic acids may e.g. comprise substitutions of nucleic acids by uncommon or synthetic or artificial nucleotides. The modified nucleic acids are characterized in that they hybridize to a nucleic acids derived from accession number NM_032982 under standard hybridization conditions applied for the respective kind or type of nucleic acid. Those of skill in the art know which hybridization conditions have to be applied to ensure specific hybridization of different types of nucleic acids or modified nucleic acids or of PNAs.

The determination of the MSI status present in samples in certain embodiments of the present invention is based on the detection of the presence or absence of mutations in the CASP2 nucleic acids. Mutation as used in the context of the present invention may comprise insertions or deletions of one or several nucleotides (or nucleotide repeats) within the specified microsatellite sequences.

With respect to the T-25 repeat disclosed herein any repeat length of the T-25 repeat in a method according to the present invention that is T-23 or smaller or is T-27 or larger (corresponding to allele lengths of 146 nt or below and 150 nt and above in a detection system as exemplified herein) is regarded as indicative of the presence of a mutation. In certain embodiments of the present invention an allele length differing from the allele length given in accession number NM_032982 by +2 or more nucleotides or −2 or more nucleotides in the oligo-T repeat located in the 3'-UTR of the named sequence, shall be regarded as being indicative for the presence of a mutation. The presence of mutations in the monomorphic T-25 repeat according to the present invention is indicative of MSI-H status.

MicroSatellite Instability (MSI) as used herein refers to a type of genetic instability present in certain human epithelial tumours, which is characterized by length variations at short repetitive DNA sequences. Throughout the text of the present invention the term MSI or MSI phenotype may be used interchangeably. In contrast hereto is the MSS (Micro Satellite Stable) phenotype. The acronym MSI-H as used herein shall denominate a phenotype being characterized by a high level of MSI according to the recommendations of the ICG-HNPCC (Boland et al. 1998).

The microsatellite status or MSI status as used in the context of the present invention refers to the presence or absence of MSI or the MSI-H phenotype. Assessment of the MSI status according to the present invention may be performed using the detection of the presence or absence of mutations in one or more microsatellites. Microsatellites that may be used for MSI typing comprise microsatellites either located intergenically or overlapping with gene-containing chromosomal regions. Gene-related microsatellites may be located in the 5' untranslated region (UTR), the coding region, the 3' UTR, or intronic regions.

Methods for the detection of the presence or absence of mutations are given below.

Medically relevant conditions associated with MSI to which the method as disclosed herein may be applied comprise any diseases associated with microsatellite instability. In one embedment of the invention such diseases are tumors. Examples of tumors associated with microsatellite instability are tumors of the anogenital tract, the colorectal tract (e.g. colorectal carcinoma, colorectal adenoma, colorectal polyps, etc.), the gastrointestinal tract (e.g. gastric cancer, carcinoma of the small intestine, polyps of the small intestine, tumors of the bile ducts, pancreatic carcinoma, etc.) and the respiratory tract, endometrial tumors (e.g. endometrial carcinoma, endometrial hyperplasia, etc.), tumors of the central nervous system (e.g. Glioblastoma multiforme, medulloblastoma, etc.), tumors of the prostate, tumors of the breast (e.g. mamma carcinoma), etc.

A sample according to the method of the present invention may comprise any sample comprising nucleic acids from tissues affected by a disorder or suspected of being affected by a disorder associated with microsatellite instability as described above. In certain embodiments the samples originate from the anogenital tract, the colorectal tract, the gastrointestinal tract, the respiratory tract and other regions where medically relevant conditions associated with microsatellite instability occur.

The samples to which a method according to the present invention may be applied may comprise various kinds of samples of clinical relevance, such as e.g. body fluids, such as e.g. blood, plasma, serum, secretions, smears, urine, semen, bile, liquor, etc. Furthermore samples may comprise stool, biopsies, cell- and tissue-samples. Biopsies as used in the context of the present invention may comprise e.g. resection samples of tumors, tissue samples prepared by endoscopic means or needle biopsies of organs.

In certain embodiments the samples may originate from the lung, the bronchus, the lower respiratory tract, the upper respiratory tract, the oral cavity, the stomach, the esophagus, the small intestine, the colon ascendens, the colon transversum, the colon descendens or the colon sigmoideum, the rectum, the anus, etc.

In certain embodiments of the present invention the sample may be a histological sample, a biopsy, or a cytological sample such as e.g. a smear, a swab, a wash, a body fluid containing. In certain embodiments of the invention the samples may comprise fixed or preserved specimens such as cytological or histological specimens. The fixation or preservation may be performed by any method known to those of skill in the art comprising alcohol fixation, embedding in paraffin, formalin fixation or the like. The samples may in certain embodiments comprise stool or samples obtained by endoscopic means such as e.g. gastroscopy, colonoscopy, etc.

For the methods according to the present invention the samples may be processed or prepared in an adequate manner to allow detection of the marker molecules under examination. In certain embodiments of the present invention such methods comprise methods for the isolation or concentration of nucleic acids from the samples. Such methods may also comprise the removal of other components of the samples such as e.g. incubation with enzymes for degradation of certain compounds such as proteins.

In one embodiment of the present invention a step for concentrating cells may be applied. This step may comprise a centrifugation, cell sorting by e.g. flow cytometry or the like, immunochemical concentration of cells (using antibodies directed against cell surface epitopes) or any other suitable method known to those of skill in the art. The concentration of cells may pertain to the concentration of cell in general or even to the concentration of specific cell types. In one embodiment the concentration may be performed via microdissection of tissue preparations. Generally samples comprising cells affected with the medically relevant conditions under investigation are suitable for application of a method according to the present invention. In one embodiment of the present invention samples are applied in which at least 10% of the total cell content is affected by the medically relevant condition under investigation. In another embodiment at least 50% of the total cell content is affected by the medically relevant condition under investigation.

In certain embodiments of the present invention the samples comprise nucleic acids originating from cells of the named regions of the body. Generally the nucleic acids are prepared from the samples by the methods known to those of ordinary skill in the art. In certain embodiments of the present invention the nucleic acids of the samples may be prepared in a way that allows for an analysis of the nucleic acids by means of respective detection method. The extraction of nucleic acids from samples may be performed by various methods and may employ a wide range of reagents or suitable commercially available kits for this purpose. Subsequently the purified nucleic acids may be subjected to suitable detection reactions such as e.g. amplification or hybridization reactions.

The detection methods for application in the present invention comprise methods for the detection of nucleic acids in general as well as methods for the detection of mutations in nucleic acids.

The detection of the presence or absence of mutations may be performed by any method suitable for the detection of mutations in nucleic acid molecules known to those of skill in the art. The methods suitable for the analysis of mutations in nucleic acids and especially of deletion or insertion mutations in nucleic acids are known to those of ordinary skill in the art. Such methods may e.g. comprise any method applied in the course of detection of the length of nucleic acids such as e.g. electrophoresis methods (e.g. gelelectrophoresis, capillaryelectrophoresis, etc.), chromatographic methods, centrifugation methods (e.g. density gradient centrifugation methods, or other suitable centrifugation methods), mass spectrometric methods, endo- or exonucleolytic cleavage methods, etc.

Detection of the nucleic acids or of mutations of the respective nucleic acids may employ any suitable reporter method. Such methods may comprise the application of reporter molecules such as colored compounds, fluorescent compounds, light emitting compounds, a radiation emitting compounds or binding structure suited for specific interaction with other molecules. Such labels may comprise FITC, biotin, streptavidin, or the like. Such reporter molecules may be applied as labels attached covalently or non-covalently to probes or primers.

It is obvious to those of skill in the art that detection of the CAT25 T-25 repeat as disclosed herein may also comprise detection on the RNA level. Under such circumstances detection of the T-25 repeat may factually comprise detection of a U-25 repeat that is equivalent to the T-25 repeat in DNA. Therefore the term "T-25 repeat" as used in the context of the present invention shall generally also refer to any complementary or reverse complementary nucleic acids (e.g. a A-25 repeat) or RNA equivalents of the T-25 repeat (i.e. a U-25 repeat) that may be employed to indirectly detect the T-25 repeat.

In certain embodiments methods for detection of mutations may comprise nucleic acid amplification reactions. Suitable amplification reactions are known to those of ordinary skill in the art and may comprise DNA based amplification as well as RNA based amplification. Amplification reactions according to the present invention may comprise PCR, LCR, NASBA, etc. The amplification reaction may be performed using one or more specific primers.

In one embodiment of the invention an amplification reaction comprises the amplification of a single nucleic acid. In another embodiment of the invention the amplification is carried out as a multiplex amplification reaction simultaneously amplifying a set of several nucleic acids. In yet another embodiment of the invention one or more polymerase chain reactions may be performed. More than one PCR may be performed sequentially or in a multiplex manner.

In one embodiment of the present invention the amplification reaction gives rise to nucleic acid fragments of 50 bp to about 500 bp length. In a preferred embodiment of the invention the length of the amplification products is from 75 bp to 300 bp in length. In a more preferred embodiment the length of the amplification product is 100 bp to 200 bp.

In one embodiment of the invention a nucleic acid amplification system as detailed in the examples herein may be applied.

However various other methods for the detection of the nucleic acids or of mutations of the nucleic acids may be applied. E.g. the allele lengths detected in the respective detection system are dependent on the parameters of the system. Those of skill in the art know how the respective allele lengths have to be amended corresponding to amendments in the detection system. Within the context of the present invention the allele lengths that may be detected with the detection system as disclosed in the examples hereto shall be cited. However any allele length determined using another system but corresponding to the named allele lengths shall be comprised when using the cited allele lengths herein.

The primer or pairs of primers for carrying out the amplification reaction in a method according to the present invention are designed in a way to give rise to amplification products of the named fragment lengths. Generally primers for use according to the present invention are nucleic acid molecules capable of hybridizing to a target nucleic acid sequence. In the present invention primers are nucleic acids capable of hybridizing to CASP2 gene nucleic acids or fragments thereof. Such primers comprise e.g. nucleic acids complementary or reverse complementary to CASP2 nucleic acids or to nucleic acids reverse complementary to CASP2 nucleic acids. The design of suitable primers may be performed using various tools for primer selection known to those of skill in the art. Example for suitable primer pairs may e.g. be selected from the following pairs:

```
1fwd 5'-CTGCCTCAAAGGGACTGC-3'           (SEQ ID NO: 1)

1rev 5'-CCTTCCCGATCCTTGATAAGT-3'        (SEQ ID NO: 2)
corresponding to an amplification
product length
of 144 b 2fwd 5'-CCTAGAAACCTTTATCCCTGCTT-3'      (SEQ ID NO: 3)

2rev 5'-GAGCTTGCAGTGAGCTGAGA-3'         (SEQ ID NO: 4)
corresponding to an amplification
product length
of 148 bp 3fwd 5'-AACCTTTATCCCTGCTTATCTGA-3'      (SEQ ID NO: 5)

3rev 5'- AGTTGGAGCTTGCAGTGAGC-3'        (SEQ ID NO: 6)
corresponding to a predicted ampli-
fication product
length of 148 bp 4fwd 5'-CCTAGAAACCTTTATCCCTGCTT-3'      (SEQ ID NO: 3)

4rev 5'-GAGCTTGCAGTGAGCTGAGA-3'         (SEQ ID NO: 4)
corresponding to a predicted ampli-
fication product
length of 149 bp 5fwd 5'-ACTTCCCAACTTCCCTGTTCTT-3'       (SEQ ID NO: 7)

5rev 5'-AGAATGGCGTGAACCCGGGA-3'         (SEQ ID NO: 8)
corresponding to a predicted ampli-
fication product
length of 144 bp 6fwd 5'-GAAACTTCCCAACTTCCCTGT-3'        (SEQ ID NO: 9)

6rev 5'-GGCGTGAACCCGGGAGTTGG-3'         (SEQ ID NO: 10)
corresponding to a predicted ampli-
fication product
length of 142 bp 7fwd 5'-AAACTTCCCAACTTCCCTGTTC-3'       (SEQ ID NO: 11)

7rev 5'-ATCATGAGGTCAGGAGATCA-3'         (SEQ ID NO: 12)
corresponding to a predicted ampli-
fication product
length of 278 bp 8fwd 5'-AACTTCCCAACTTCCCTGTTC-3'        (SEQ ID NO: 13)

8rev 5'-ATCATGAGGTCAGGAGATC-3'          (SEQ ID NO: 14)
corresponding to a predicted ampli-
fication product
length of 277 bp 9fwd 5'-CTTCCCAACTTCCCTGTTCTT-3'        (SEQ ID NO: 15)

9rev 5'-GGATCATGAGGTCAGGAGA-3'          (SEQ ID NO: 16)
corresponding to a predicted ampli-
fication product
length of 277 bp 10fwd 5'-ACCTAGAAACCTTTATCCCTGCTT-3'    (SEQ ID NO: 17)

10rev 5'-CATGAGGTCAGGAGATCAA-3'         (SEQ ID NO: 18)
corresponding to a predicted ampli-
fication product
length of 305 bp
```

```
11fwd 5'-CCTAGAAACCTTTATCCCTGCT-3'    (SEQ ID NO: 19)

11rev 5'-TTTGGGAGGCTGAGGTGGGT-3'     (SEQ ID NO: 20)
corresponding to a predicted ampli-
fication product
length of 328 bp 12fwd 5'-AACCTAGAAACCTTTATCCCTGCT-3' (SEQ ID NO: 21)

12rev 5'-ACTTTGGGAGGCTGAGGTGGG-3'    (SEQ ID NO: 22)
corresponding to a predicted ampli-
fication product
length of 332 bp
```

Those of skill in the art know how primers may be selected and could find other alternatives for primer pairs for inclusion in a kit according to the present invention. Moreover the given primers may be used in combinations other than those given. Thus the forward primers of any of the given primer pairs may be used with a suitable reverse primer either selected from any one of the given primer pairs or a completely different primer. Those of skill in the art know how to choose the suitable primer pairs. In certain embodiments the amplimers length may be above 200 bp or below 100 bp depending on the conditions of the amplification.

In certain embodiments the probes or primers may be detectably labeled. Suitable labels may be colored compounds, fluorescent compounds, light emitting compounds, a radiation emitting compounds or binding structure suited for specific interaction with other molecules. Such labels may comprise FITC, biotin, streptavidin, or the like.

In certain embodiments of the present invention the detection of mutations in the T-25 repeat of the Caspase-2 gene may be used for diagnostic purposes in combination with detection of mutations in other microsatellite regions. Generally any other microsatellite region known to be associated with MSI status may be employed. In certain embodiments of the invention the Caspase-2 T-25 microsatellite may be used in combination with the microsatellites from the BAT25 and/or BAT26 genes.

Furthermore a combination of the T-25 repeat with BAT40 microsatellite may be applied. In one embodiment of the present invention detection of mutations in the T-25 repeat of the Caspase-2 gene may be combined with detection of mutations of all or some genes included in the Bethesda-Panel (D2S123, D17S250, D5S346). In certain embodiments employing combinations of two or several microsatellites for diagnosis examination of normal tissue may be performed. Further more suitable combinations for determination of microsatellite status may comprise determination of mutations in one or more of the microsatellite regions selected from a group comprising: CASP2, BAT25, BAT26, BAT40, APdelta3, U79260, PPP3CA, CTNNB1, GTF2E1 and others. Recently published microsatellite markers that may especially be suitable for a combination with CAT25 are for example NR-21 (Suraweera et al. 2002, Bacher et al. 2004), NR-22 (Suraweera et al. 2002), NR-24 (Suraweera et al. 2002, Bacher et al. 2004), Mono27 (Bacher et al. 2004).

Those of skill in the art know how suitable primers for performing the reaction of the present invention can be selected. Suitable primer pairs for amplification of the microsatellites within some of the markers named above comprise:

```
BAT40    fwd    ATTAACTTCCTACACCACAAC
                (SEQ ID NO: 23)
         rev    GTAGAGCAAGACCACCTTG
                (SEQ ID NO: 24)

D2S123   fwd    AAACAGGATGCCTGCCTTTA
                (SEQ ID NO: 25)
         rev    GGACTTTCCACCTATGGGAC
                (SEQ ID NO: 26)

D17S250  fwd    GGAAGAATCAAATAGACAAT
                (SEQ ID NO: 27)
         rev    GCTGGCCATATATATATTTAAACC
                (SEQ ID NO: 28)

D5S346   fwd    ACTCACTCTAGTGATAAATCG
                (SEQ ID NO: 29)
         rev    AGCAGATAAGACAGTATTACTAGTT
                (SEQ ID NO: 30)

GTF2E1   fwd    CCCTTCCTTGCTGTCACTACA
                (SEQ ID NO: 31)
         rev    TGAACCCAGGAGGCAGAG
                (SEQ ID NO: 32)

PPP3CA   fwd    GTCGCAGCACTAAAAATGGA
                (SEQ ID NO: 33)
         rev    GAAGGGCATTCAAGCACACT
                (SEQ ID NO: 34)

CTNNB1   fwd    AATTTAGCAAACCCTAGCCTTG
                (SEQ ID NO: 35)
         rev    AAGAGCTACTTCAAAGCAAGCA
                (SEQ ID NO: 36)

APdelta3 fwd    AGCAGTGGCAGCTCAGAAAT
                (SEQ ID NO: 37)
         rev    GCCTCTTGATCACGTCCAA
                (SEQ ID NO: 38)

U79260   fwd    TTTGTTATATCCCATTAGGTGCC
                (SEQ ID NO: 39)
         rev    AGCCTGGTGACAGAGTGAGAC
                (SEQ ID NO: 40)
```

Generally the advantage of using a combination of marker molecules over the use of only on single marker is the increased sensitivity. A large number of markers is known to those of skill in the art that may be reliably be used for detection the presence of MSI in the presence of matched normal tissue. One disadvantage of such markers for testing is the need for additional testing of the matched normal tissue and thus increased cost. A combination of certain well chosen MSI markers together with CAT25 may enable for very high sensitivity for detection of MSI and a nevertheless reduced testing procedure. Especially CAT25 may be used for reliable detection of MSI status even in the absence of matched normal tissue nonetheless giving sensitivity of up to 100%. Due to these properties of the CAT25, combinations of the CAT25 repeat with other known marker molecules could be used without including normal tissue into the diagnostic testing procedure. Such combinations comprise for example the following:

CAT25, BAT25
CAT25, BAT26
CAT25, NR-21
CAT25, NR-24
CAT25, MONO27
CAT25, BAT25, BAT26
CAT25, BAT25, MONO27
CAT25, BAT25, NR-21
CAT25, BAT25, NR-24
CAT25, BAT26, MONO27
CAT25, BAT26, NR-21
CAT25, BAT26, NR-24

CAT25, NR-21, MONO27
CAT25, NR-21, NR-24
CAT25, MONO27, NR-24

Possible combinations that may be applied are given in the examples below. Those of skill in the art know several other possible combination of suitable MSI marker molecules.

Another aspect of the present invention is a kit for performing the methods disclosed herein. A kit according to the present invention comprises one or more binding agents specifically recognizing a CASP2 nucleic acid. In certain embodiments of the present invention the kits may be provided as in-vitro diagnostic devices.

An in-vitro diagnostic device is a kit that is intended for assessment of diagnosis of a medically relevant condition from human or animal body samples. In certain embodiments of the invention an in-vitro diagnostic device shall be any device that falls in the scope of the definition of in-vitro diagnostic medical device as given in the directive 98/79 EC under Article 1 (b):

'in vitro diagnostic medical device' means any medical device which is a reagent product, calibrator, control material, kit, instrument, apparatus, equipment, or system, whether used alone or in combination, intended by the manufacturer to be used in vitro for the examination of specimens, including blood and tissue donations, derived from the human body, solely or principally for the purpose of providing information concerning a physiological or pathological state; or concerning a congenital abnormality; or to determine the safety and compatibility with potential recipients; or to monitor therapeutic measures.'

In vitro diagnostic device shall also apply to U.S. Class I IVD and generally to in-vitro diagnostic devices that are provided without Claims regarding their diagnostic performance. Therefore also any kind of ASR or the like shall be understood to be an in-vitro diagnostic device as used herein. In one embodiment of the present invention the in-vitro diagnostic device is characterized by solid phase fixed detection reagents specific for a marker molecules.

The binding agents included in the kits and in-vitro diagnostic devices may comprise nucleic acid molecules of any kind and nature, such as e.g. polynucleotides or fragments thereof. Polynucleotides may for example include single-stranded (sense or antisense) or double-stranded molecules, and may be DNA (genomic, cDNA or synthetic) or RNA. RNA molecules comprise as well hnRNA (containing introns) as mRNA (not containing introns). According to the present invention the polynucleotides included in a kit may also be linked to any other molecules, such as support materials or detection marker molecules, and may, but need not, contain additional coding or non-coding sequences. The nucleic acids provided as parts of a kit according to the present invention may also comprise any kind of synthetic or modified nucleic acids such as synthetic or modified polynucleotides or fragments thereof, peptide nucleic acids (PNAs) or the like. Specific types of such synthetic or modified nucleic acids are known to those of skill in the art. In certain embodiment synthetic nucleic acids may comprise uncommon or artificial nucleosides (e.g. with altered sugar components or with altered purine or pyrimidine components, etc.) or nucleotides (e.g. thiophosphate or phosphorothioate nucleotides) or analogues thereof. Such alterations may e.g. comprise the introduction of labels such as radioactive labels (e.g. as radiation emitting radioisotopes $^{32}P$, $^{35}S$, $^{14}C$, $^{3}H$, etc.), introduction of colored or fluorescent (e.g. maleimide, iodoacetamide, etc.) components or of binding moieties such as biotin or the like into the nucleic acids. In certain embodiments the introduction of thiol groups in the sugar and or the pyrimidine or purine (e.g. 4-thiouridine or the like) component may be of certain advantage for the subsequent detection reaction. Reactive forms of fluorescent dyes such as e.g. Oregon Green 488, Rhodamine Green, Rhodamine Red, Texas Red, fluorescein, tetramethylrhodamine, biotin-, DSB biotin and DNP succinimidyl esters may be used for labeling of the nucleic acids for use in the kits and in-vitro diagnostic devices according to the present invention. As the case may be the labels may be couples via spacers to the nucleic acids. Such spacers comprise e.g. aminohexanoyl spacers or the like. In certain embodiments of the present invention the nucleic acids are modified in a way to allow for FRET analysis of the hybridization reaction. the methods for the provision of modified and altered nucleic acids are known to those of ordinary skill in the art. The above examples of modifications, alterations and labels are for exemplification only and are not intended to restrict the scope of the invention. Various other modifications and labels for nucleic acids are known to those of skill in the art. In certain embodiments of the invention any of the methods known in the art may be applied to nucleic acids inclusion into a kit or in-vitro diagnostic device according to the present invention.

In certain embodiments of the present invention the nucleic acids may be provided as probes or primers for performing nucleic acid hybridization or nucleic acids amplification reactions. The probes and primers may be of any kind and nature known to those of skill in the art. Preferably primers are of a size of 5 nt to 50 nt, more preferably of a size of 10 nt to 35 nt and most preferably of a size of 15 nt to 25 nt. Those of skill in the art know how to select suitable primers for nucleic acid amplification reaction. The size of the primers is dependent on amplification conditions as well as on the sequence of the nucleic acid to be amplified. Therefore under certain circumstances the larger primers may be preferred, whereas under standard amplification conditions known to those of skill in the art the primer sizes as preferred above may be applicable.

In certain embodiments of the present invention further components may be included in a kit or in-vitro diagnostic device according to the present invention. Such components may e.g. comprise reagents useful or necessary in an nucleic acid amplification reaction comprising one or more polymerase enzymes, substrates for the amplification reaction, buffers and/or activators or the like.

Furthermore in certain embodiment the kits and in-vitro diagnostic devices may comprise compounds for use in the conditioning, purification or concentration of samples or nucleic acids comprising solid phases (e.g. particles, beads, magnetic-beads in any form such as e.g. as spin columns, chromatographic columns or the like), devices for centrifugation or chromatography, ready to use tubes and/or filters and/or membranes. Also reagents and buffers suitable for the preparation of genomic DNA from given samples (e.g. from cells, cell suspensions, tissues and/or stool and/or blood and/or sputum) may be (additionally) included in certain embodiments of the present invention. In certain further embodiments of the kits and in-vitro diagnostic devices packaging of said kits and in-vitro diagnostic devices according to the present invention may be suitable for use in automated systems.

Each of the above features of the kits and in-vitro diagnostic devices may apply to the kits of the present invention alone or in a combination with each of the other features, in a combination with some of the other features (more than one!) or even in a combination with all the other given features.

In one embodiment of the present invention a kit may comprise a pair of primers for performance of an amplification reaction. The pair of primers may give rise to amplimers of a length of 100 pb to 200 bp. The pair of primers may in certain embodiments of the invention have sequences selected from the following pairs of primers (SEQ ID NOs: 1-22):

```
1fwd 5'-CTGCCTCAAAGGGACTGC-3'

1rev 5'-CCTTCCCGATCCTTGATAAGT-3'
corresponding to an amplification product length
of 144 bp 2fwd 5'-CCTAGAAACCTTTATCCCTGCTT-3'

2rev 5'-GAGCTTGCAGTGAGCTGAGA-3'
corresponding to an amplification product length
of 148 bp 3fwd 5'-AACCTTTATCCCTGCTTATCTGA-3'

3rev 5'- AGTTGGAGCTTGCAGTGAGC-3'
corresponding to a predicted amplification product
length of 148 bp 4fwd 5'-CCTAGAAACCTTTATCCCTGCTT-3'

4rev 5'-GAGCTTGCAGTGAGCTGAGA-3'
corresponding to a predicted amplification product
length of 149 bp 5fwd 5'-ACTTCCCAACTTCCCTGTTCTT-3'

5rev 5'-AGAATGGCGTGAACCCGGGA-3'
corresponding to a predicted amplification product
length of 144 bp 6fwd 5'-GAAACTTCCCAACTTCCCTGT-3'

6rev 5'-GGCGTGAACCCGGGAGTTGG-3'
corresponding to a predicted amplification product
length of 142 bp 7fwd 5'-AAACTTCCCAACTTCCCTGTTC-3'

7rev 5'-ATCATGAGGTCAGGAGATCA-3'
corresponding to a predicted amplification product
length of 278 bp 8fwd 5'-AACTTCCCAACTTCCCTGTTC-3'

8rev 5'-ATCATGAGGTCAGGAGATC-3'
corresponding to a predicted amplification product
length of 277 bp 9fwd 5'-CTTCCCAACTTCCCTGTTCTT-3'

9rev 5'-GGATCATGAGGTCAGGAGA-3'
corresponding to a predicted amplification product
length of 277 bp 10fwd 5'-ACCTAGAAACCTTTATCCCTGCTT-3'

10rev 5'-CATGAGGTCAGGAGATCAA-3'
corresponding to a predicted amplification product
length of 305 bp 11fwd 5'-CCTAGAAACCTTTATCCCTGCT-3'

11rev 5'-TTTGGGAGGCTGAGGTGGGT-3'
corresponding to a predicted amplification product
length of 328 bp 12fwd 5'-AACCTAGAAACCTTTATCCCTGCT-3'

12rev 5'-ACTTTGGGAGGCTGAGGTGGG-3'
corresponding to a predicted amplification product
length of 332 bp
```

Those of skill in the art know how primers may be selected and could find other alternatives for primer pairs for inclusion in a kit according to the present invention. Moreover the given primers may be used in combinations other than those given. Thus the forward primers of any of the given primer pairs may be used with a suitable reverse primer either selected from any one of the given primer pairs or a completely different primer. Those of skill in the art know how to choose the suitable primer pairs. In certain embodiments the amplimer length may be above 200 bp or below 100 bp depending on the conditions of the amplification.

A kit according to the present invention may as the case may be also comprise one or more probes for testing of polymorphic typing markers. Such polymorphic markers may be employed as controls to ensure sample identity. A list of polymorphic typing markers for the application is provided in FIG. 10. Such polymorphic markers may e.g. be found in databases such as STRBase at www.cstl.nist.gov/biotech/strbase/

In certain embodiments of the present invention the kit comprises additionally compounds for detection of mutations in other genes. Such genes may be selected from a group comprising but not limited to CAT25, BAT25, BAT26, BAT40, APdelta3, U79260, PPP3CA, CTNNB1, GTF2E1.

A further aspect of the present invention pertains to the use of probes and primers specific for the CASP2 gene disclosed under accession number NM_032982. The probes and primers may be complementary or reverse complementary to the nucleic acid sequence given under said accession number. The probes or primers may be nucleic acids of any kind and nature as defined above.

Manufacturing of a kit or in-vitro diagnostic device as used in this context refers to any action intended to provide a kit or in-vitro diagnostic device as defined above on a commercial basis to customers. Such action comprise actions such as manufacturing of parts for a finished kit or in-vitro diagnostic device, assembling of parts into a kit, repackaging, re-labelling and/or refurbishing of kits or in-vitro diagnostic devices.

In this respect the present invention also refers to a method for development of kits and in-vitro diagnostic devices making use of the probes and primers specific for the CASP2 gene disclosed under accession number NM_032982. Said probes and primers may in this respect either be used as an aid in the development of the kits and in-vitro diagnostic devices or be part of the kits and in-vitro diagnostic devices under development.

Development as used in the context of the present invention shall pertain to all design and development activities performed for enabling a manufacturer for controlled production of a finished kit or in-vitro diagnostic device intended for commercial distribution or sale of said kit or in-vitro diagnostic device. Development of kits and in-vitro diagnostic devices as used in the context of the present invention accordingly shall pertain to all activities in connection with the design and development, design- and development-verification, design- and development-validation, assessment of performance data, assessment of safety and effectiveness data of kits and in-vitro diagnostic devices. In one embodiment development shall pertain to the testing of design- and development-outputs of kits and in-vitro diagnostic devices for suitability regarding the proposed intended use. Intended use in this respect shall be understood as the detection or diagnostic purposes for which the kit or in-vitro diagnostic device shall be applied.

The method of development of kits and in-vitro diagnostic devices as disclosed herein may employ the probes and primers as disclosed herein in all stages of the design, development, verification, validation, provision of data for regulatory submission and clearance/approval, or may employ the probes and primers as disclosed herein only in one or some of the named steps of kit or in-vitro diagnostic device design and development. In one embodiment of the invention the method of development of the kits or in-vitro diagnostic devices according to the present invention is a method for design and development of said kits and in-vitro diagnostic devices, wherein the probes and primers as disclosed herein are used for design and development verification and/or validation. In another embodiment of the invention the method of development of kits and in-vitro diagnostic devices is a method for provision of data for regulatory submission and clearance/approval of kits and/or in-vitro diagnostic devices before national or regional regulatory authorities and/or national or regional regulatory (notified) bodies, wherein the probes and primers as disclosed herein are used for the provision of technical data, performance data or safety and effectiveness data regarding the kit or in-vitro diagnostic device. In a further embodiment of the invention the method of development of kits and in-vitro diagnostic devices is a method where the latter methods are combined.

A further aspect of the present invention is a system for the assessment of the MSI status of medically relevant conditions based on the detection of mutations in the T-25 repeat of the 3'-UTR of the CASP2 gene. The system according to the present invention may comprise several components including but not limited to at least one component for detection and/or evaluation of signals levels and/or intensities, wherein the signals are indicative for the presence or absence of mutations in the T-25 repeat of the 3'-UTR of the CASP2 gene, at least one component for correlation of the detected and/or evaluated signal levels and/or intensities to clinical date, wherein the clinical data pertain to expectation for success and/or effectiveness of therapeutic measures applied to the medically relevant condition under investigation.

The system may in certain embodiments of the invention be computer aided.

The component for detection and/or evaluation of signals levels and/or intensities, wherein the signals are indicative for the presence or absence of mutations in the T-25 repeat of the 3'UTR of the CASP2 gene may comprise devices of any kind and nature applied for analysis of the results of the methods disclosed herein for the detection of mutations. In certain embodiments the component may be a device applicable for detection of fluorescence signals, a device applicable for the detection of absorption of light or the like.

The component for correlation of the detected and/or evaluated signal levels and/or intensities to clinical date, wherein the clinical data pertain to expectation for success and/or effectiveness of therapeutic measures applied to the medically relevant condition under investigation may comprise a storage means for storing and/or providing information on expectation for success and/or effectiveness of therapeutic measures in correlation to the presence or absence of mutations in the T-25 repeat of the 3'-UTR of the CASP2 gene. Such storage means may be e.g. a database, a library, a card index or any other suitable means. The storage means may be provided digitally or analogous. Storage means for application in a system according to the present invention may comprise e.g. computers micro (chips), any digital storage medium, paper-based formats, magnetically based storage media, photographic storage media, micro-fiche or in any other suitable format.

The system may in certain embodiments of the invention be used for a method for assessment of adequate therapy of individuals. One further aspect of the present invention is therefore a computer implemented method for building a strategy for therapy of medically relevant conditions associated with MSI comprising i) comparing data representing the presence or absence of mutations in the T-25 repeat located in the 3'-UTR of the CASP2 gene to clinical data comprising information on the presence or absence of mutations in said T-25 repeat and information about the patients disease course and outcome by a comparing means; ii) building up subgroups of data representing individuals according to the presence or absence of mutations and giving subgroups to an assessment means; and iii) assessing the comparison based on the subgroups of data by the assessment means and giving the assessment from the assessment means to a therapy tailoring means, the therapy tailoring means tailoring an adequate therapy for the individuals according the assessment.

One further aspect of the present invention are nucleic acids for performing a method of assessment of the MSI status of medically relevant conditions. Such nucleic acids may comprise probes and primers useful for detection of the presence or absence of mutations in the T-25 repeat located in the 3'-UTR of the CASP-2 gene.

In one embodiment of the present invention nucleic acids may comprise e.g. (pairs of) primers for performance of an amplification reaction. The primers may give rise to amplimers of a length of e.g. 100 pb to 200 bp. The pair of primers may in certain embodiments of the invention have sequences selected from the following pairs of primers (see also FIG. 11, SEQ ID NOs: 1-22):

```
1fwd 5'-CTGCCTCAAAGGGACTGC-3'

1rev 5'-CCTTCCCGATCCTTGATAAGT-3'
corresponding to an amplification product length
of 144 bp 2fwd 5'-CCTAGAAACCTTTATCCCTGCTT-3'

2rev 5'-GAGCTTGCAGTGAGCTGAGA-3'
corresponding to an amplification product length
of 148 bp 3fwd 5'-AACCTTTATCCCTGCTTATCTGA-3'

3rev 5'- AGTTGGAGCTTGCAGTGAGC-3'
corresponding to a predicted amplification product
length of 148 bp 4fwd 5'-CCTAGAAACCTTTATCCCTGCTT-3'

4rev 5'-GAGCTTGCAGTGAGCTGAGA-3'
corresponding to a predicted amplification product
length of 149 bp 5fwd 5'-ACTTCCCAACTTCCCTGTTCTT-3'

5rev 5'-AGAATGGCGTGAACCCGGGA-3'
corresponding to a predicted amplification product
length of 144 bp 6fwd 5'-GAAACTTCCCAACTTCCCTGT-3'

6rev 5'-GGCGTGAACCCGGGAGTTGG-3'
corresponding to a predicted amplification product
length of 142 bp 7fwd 5'-AAACTTCCCAACTTCCCTGTTC-3'

7rev 5'-ATCATGAGGTCAGGAGATCA-3'
corresponding to a predicted amplification product
length of 278 bp 8fwd 5'-AACTTCCCAACTTCCCTGTTC-3'

8rev 5'-ATCATGAGGTCAGGAGATC-3'
corresponding to a predicted amplification product
length of 277 bp
```

-continued

```
 9fwd 5'-CTTCCCAACTTCCCTGTTCTT-3'

9rev 5'-GGATCATGAGGTCAGGAGA-3'
corresponding to a predicted amplification product
length of 277 bp 10fwd 5'-ACCTAGAAACCTTTATCCCTGCTT-3'

10rev 5'-CATGAGGTCAGGAGATCAA-3'
corresponding to a predicted amplification product
length of 305 bp 11fwd 5'-CCTAGAAACCTTTATCCCTGCT-3'

11rev 5'-TTTGGGAGGCTGAGGTGGGT-3'
corresponding to a predicted amplification product
length of 328 bp 12fwd 5'-AACCTAGAAACCTTTATCCCTGCT-3'

12rev 5'-ACTTTGGGAGGCTGAGGTGGG-3'
corresponding to a predicted amplification product
length of 332 bp
```

Those of skill in the art know how primers may be selected and could find other alternatives for primer pairs for inclusion in a kit according to the present invention. Moreover the given primers may be used in combinations other than those given. Thus the forward primers of any of the given primer pairs may be used with a suitable reverse primer either selected from any one of the given primer pairs or a completely different primer. Those of skill in the art know how to choose the suitable pri8merr pairs. In certain embodiments the amplimers length may be above 200 bp or below 100 bp depending on the conditions of the amplification.

The present invention provides compounds and methods for improved performance of assessment of MSI status in medically relevant conditions associated with MSI.

The following is intended solely as an exemplification of the invention and is not intended to restrict the scope of the invention.

EXAMPLE 1

Assessment of Instability at the CAT25 Mononucleotide Repeat in MSI-H and MSS Colorectal Carcinomas Sample Preparation and DNA Extraction Genomic DNA was isolated from formalin-fixed, paraffin-embedded CRC specimens (n=117) after manual microdissection using a commercially available kit (DNeasy Tissue KIT, Qiagen, Hilden, Germany). For the evaluation of allele distribution, genomic DNA was isolated from non-diseased tissue samples of non-related donors (n=200).

Microsatellite Instability Analysis and Multiplex PCR

Typing of microsatellite instability was carried out using the standard ICG-HNPCC marker panel as described (Boland et al. 1998, Sutter et al. 1999). Tumors were classified as highly microsatellite unstable (MSI-H) if more than 30% of the markers displayed instability, low microsatellite unstable (MSI-L) with instability in only one marker, or microsatellite stable (MSS) if no instabilities were detected.

PCR primers for the amplification of CAT25 (fwd 5'-CCTAGAAACCTTTATCCCTGCTT-3' SEQ ID NO: 3; and rev 5'-GAGCTTGCAGTGAGCTGAGA-3', SEQ ID NO: 4) were designed using the "Primer3" software (Whitehead, MIT, USA). Sense PCR primers were 5' labeled with fluorescein isothiocyanate (FITC; BAT26 and CAT25) or HEX fluorescent dye (BAT25), respectively. Multiplex PCR was carried out in a total reaction volume of 25 µl using a final concentration of 200 µM dNTPs, 12.5 pM of each primer, 1×PCR buffer (20 mM Tris-HCl, pH 8.4, 50 mM KCl), 1.5 mM $MgCl_2$, and 0.75 units of Taq DNA polymerase (GIBCO/BRL, Eggenstein, Germany). 50 ng genomic DNA was used as a template. Reaction mixes were subjected to the following steps: initial denaturation at 94° C. for 5 min, followed by 38 cycles of denaturation at 94° C. for 30 s, annealing at 55° C. for 30 s, extension at 72° C. for 1 min, and a final extension step at 72° C. for 7 min PCR products were electrophoresed on 2% agarose gels.

Fragment Analysis and Statistical Evaluation

For fragment analysis, 2 µl of appropriately diluted PCR products were mixed with 12 µl of formamide and 0.2 µl ROX500 length standard (Applied Biosystems, Darmstadt, Germany). Dilutions were separated on ABI PRISM® 3100 Genetic Analyzer (Applied Biosystems) using Filter Set D. Size, height, and profiles of microsatellite peaks were analyzed using the GeneScan 3.7 software (Applied Biosystems). The PCR product with the largest peak area was defined as the main allele. For each tumor, the number of shifted bases in comparison to the corresponding normal mucosa was counted, and mean basepair deletions were calculated for each mononucleotide microsatellite marker. Statistical analysis and graphical displays (Box Whisker plot, histogram) were performed by using the Statistica 6.0 software (StatSoft, Tulsa, USA).

During our search for microsatellites located in 3' untranslated regions (UTRs) of cancer-relevant genes, we identified a $T_{25}$ repeat (SEQ ID NO: 96) located within the 3' UTR of the Caspase 2 (CAT25) gene. To test the diagnostic sensitivity and specificity of the CAT25, colorectal cancer specimens previously typed for their microsatellite status using the standard ICG-HNPCC marker panel (Boland et al. 1998) as MSI-H (n=57) or non-MSI-H (MSI-L, n=10; MSS, n=50) were analyzed for instability at the CAT25 locus. In all MSI-H CRCs, mutations of CAT25 were observed (compare the details given in FIG. 1).

FIG. 1 shows the mutations of microsatellite markers in MSI-H CRC. Black circles in this figure indicate mutated microsatellites, open circles indicate wild type microsatellites, n.a. indicates, that sample was not analyzable.

Thus, CAT25 surpassed the ICG-HNPCC standard markers with the highest mutation frequencies, BAT25 and BAT26, in diagnostic sensitivity for the MSI-H phenotype (mutations in 56/57 cases each). In contrast, no mutations were observed in any of the MSS or MSI-L CRC samples (not shown).

Distribution of CAT25 Allele Lengths in Normal Tissue Specimens

Figure 4:
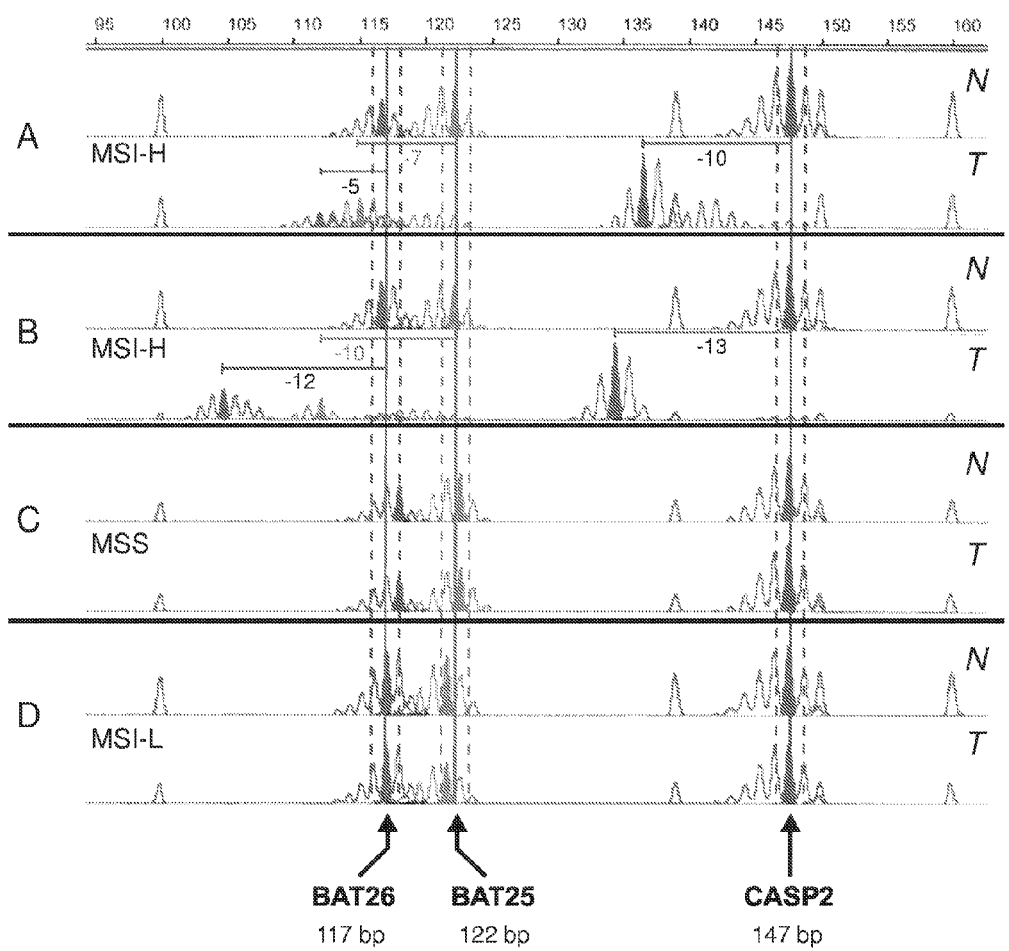
FIG. 4: Distribution of product lengths of amplification products from multiplex PCR for BAT25, BAT26, CASP2 (CAT25): Multiplex PCR amplification of BAT26, BAT25, and CASP2 from two MSI-H CRCs (A and B), one MSS CRC(C), and one MSI-L CRC (D). PCR products are displayed for BAT26 (average relative product length 117 bp), BAT25 (122 bp), and CASP2 (147 bp). Filled peaks span the largest area and are defined as main product length. The range of product lengths observed in normal DNA of healthy individuals is indicated by dashed lines for each marker. Shifts were observed exclusively in MSI-H tumours, shift lengths are denoted above the corresponding product peaks. For details see Example 1.

In order to further reduce the workload required for microsatellite typing, the applicability of CAT25 for MSI analysis without corresponding normal tissue was evaluated. For this purpose, markers with monomorphic allele distribution are required. To test whether CAT25 fulfilled this criterion, the allele length distribution was determined in normal DNA (non-tumorous tissue specimens and peripheral blood) of 200 non-related Caucasian donors. The PCR product most frequently observed (128 individuals, 64.0%) was 147 bp in length (referred to as wild type allele), a product of 146 bp was detected in 18 cases (9.0%), a product of 148 bp in 54 cases (27.0%). No additional alleles shorter than 146 bp or longer than 148 bp in length were observed. Hence, CAT25 was found to be quasi-monomorphic (wt±1 bp, according to the definition of Hoang et al. 1997 and Ichikawa et al. 2001) in 200 normal DNA samples from Caucasian individuals. A comparison of product lengths obtained from normal DNA samples and MSI-H CRC samples is depicted in FIG. 3. In FIG. 3 the distribution of CASP2, BAT25, and BAT26 product lengths in colonic tumours is displayed. Relative product lengths observed in MSI-H CRCs (shaded columns) and non-tumorous DNA samples (black columns). About two-thirds of the tested normal DNA collective (mainly from Caucasian donors) presented with a main CASP2 product length of 147 bp. Because no variations exceeding one nucleotide were observed, the detection of MSI was possible in all but one case without the analysis of corresponding normal tissue. FIG. 4 gives the distribution of product lengths of amplification products from multiplex PCR for BAT25, BAT26, CAT25 from two MSI-H CRCs (A and B), one MSS CRC(C), and one MSI-L CRC (D). PCR products are displayed for BAT26 (average relative product length 117 bp), BAT25 (122 bp), and CASP2 (147 bp). Filled peaks span the largest area and are defined as main product length. The range of product lengths observed in normal DNA of healthy individuals is indicated by dashed lines for each marker. Shifts were observed exclusively in MSI-H tumours, shift lengths are denoted above the corresponding product peaks. For details see Example 1.

In addition, normal DNA samples from donors of African (n=102) and Asian origin were analyzed for the CAT25 allele length distribution. Also here, no alleles shorter than 146 bp or longer than 148 bp were detected, arguing in favor of a monomorphic allele pattern at the CAT25 locus in all populations irrespective of their ethnic origin. This is in sharp contrast to the standard mononucleotide markers BAT25 and BAT26 which exhibited shorter alleles in about 25% of African individuals. An overview of allele length distributions of CAT25, BAT25, and BAT26 is provided in FIG. 2. FIG. 2 displays the main product lengths of BAT25, BAT26, and CAT25 observed in normal DNA samples from donors of different ethnic origin. Variant BAT25 and BAT26 alleles which might lead to misclassification of MSI were observed in 26.5% and 21.6%, respectively. CAT25 products ranged between 146 bp and 148 bp in all tested individuals (n=381). Gray boxes—range of product lengths observed in normal DNA from Caucasian individuals.

Combination of CAT25, BAT25, and BAT26 in a multiplex PCR approach MSI analysis without normal control tissue requires a threshold that defines instability at a certain microsatellite locus. For CAT25, no products longer than 148 bp or shorter than 146 bp were observed in DNA samples from non-tumorous or MSS CRC specimens. Therefore, any product length<146 bp or >148 bp was defined as indicative of MSI at the CAT25 locus. In one MSI-H tumor (HD-35), CAT25 product amplified from tumor DNA was 146 bp (corresponding to a shift of −1 nucleotide when compared to normal control tissue of the same patient). In this case, the MSI-H phenotype would have been missed by the amplification of CAT25 from tumor tissue alone. Therefore, we established a multiplex protocol that combines CAT25, BAT25, and BAT26 in one PCR. By using this approach, 117/117 (100%) CRC samples were classified correctly as MSI-H or non-MSI-H. Examples of fragment patterns obtained by this multiplex approach are presented in FIG. 4.

Mean Basepair Deletion of CAT25, BAT25, and BAT26 in MSI-H CRC

The MSI-H phenotype is detected more easily if it is accompanied by large deletions and/or insertions at the microsatellite loci used for MSI typing. For BAT26, average basepair deletion was the highest with 8.8 bp (SD±3.2), followed by CAT25 (8.1 bp±2.9) and BAT25 (6.0 bp±2.3). Consequently, the novel CAT25 marker ranged between the mononucleotide markers BAT26 and BAT25 regarding the average basepair deletion.

EXAMPLE 2

Assessment of Instability at the CAT25 Mononucleotide Repeat in Colorectal Adenomas of the Microsatellite Instability Phenotype Sample Preparation and Microsatellite Analysis Preparation of Colorectal Adenomas, DNA Extraction, and Microsatellite analysis were performed as described in Example 1.

Fourteen colorectal adenomas which were previously typed as MSI-H by using the standard ICG-HNPCC marker panel (Boland et al. 1998) were analyzed for shifts at the T25 mononucleotide repeat located in the 3'-UTR of the CASP2 gene (CAT25). Mutation frequency of the microsatellite loci CAT25, BAT25, and BAT26 are depicted in Table 1.

TABLE 1

Mutation frequency in MSI-H colorectal adenomas

| | mutation frequency (%) |
|---|---|
| CAT25 | 13/14 (92.9) |
| BAT25 | 11/14 (78.6) |
| BAT26 | 11/13 (84.6) |

Mean shift lengths observed in colorectal adenomas were 6.0 for CAT25, 4.6 for BAT25, and 5.0 for BAT26. Thus, CAT25 exceeded BAT25 and BAT26 in the detection of MSI-H colorectal carcinomas concerning the sensitivity and the mean shift length.

EXAMPLE 3

Assessment of Instability at the CAT25 Mononucleotide Repeat in Extracolonic Malignancies of the Microsatellite Instability Phenotype (Endometrial Cancer, Ovarian Cancer, Urothelial Cancer)

Sample Preparation and Microsatellite Analysis

Figure 5:
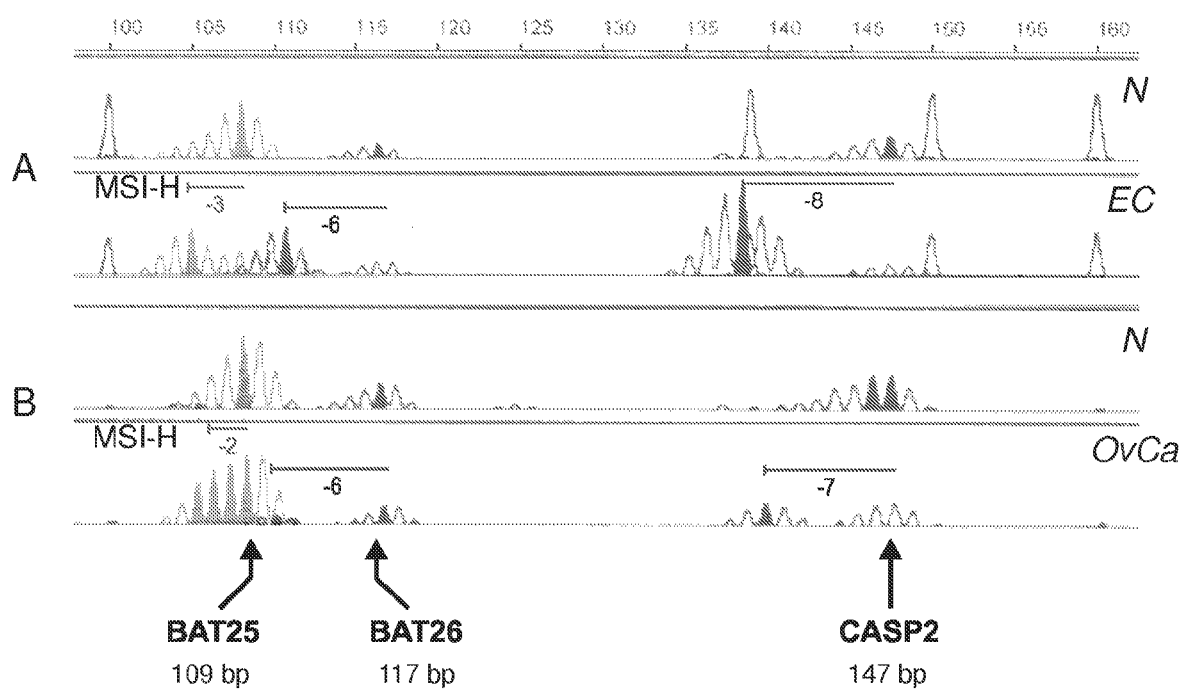
FIG. 5: Distribution of CASP2, BAT25, and BAT26 product lengths in of extracolonic MSI tumours: Relative product lengths observed in multiplex PCR amplification of BAT26, BAT25, and CASP2 from two extracolonic MSI-H tumors are displayed. Products amplified from an MSI-H endometrial cancer (A) and an MSI-H ovarian cancer (B). PCR products are displayed for BAT26 (average relative product length 117 bp), BAT25 (109 bp), and CASP2 (147 bp). Filled peaks span the largest area and are defined as main product length. Shifts were observed exclusively in MSI-H tumours, shift lengths are denoted above the corresponding product peaks. Largest shift lengths are observed for CASP2. For details see Example 3.

Preparation of tumor tissue samples, DNA extraction, and microsatellite analysis were performed as described in Example 1. For the amplification of BAT25, an alternative antisense oligonucleotide primer (5'-TATGGCTCTAAAAT-GCTCTGTTC-3', SEQ ID NO: 41) was used, resulting in a mean main product length of 109 nt (FIG. 5).

Extracolonic malignancies (n=7) which were previously typed as MSI-H by using the standard ICG-HNPCC marker panel (Boland et al. 1998) were analyzed for shifts at the T25 mononucleotide repeat located in the 3'-UTR of the CASP2 gene. For amplification, a multiplex system combining CASP2, BAT25, and BAT26 in one reaction was applied (detailed description in Example 1). By using this approach, 7 (100%) out of 7 extracolonic tumour lesions were classified correctly as MSI-H. These lesions comprised endometrial cancer (n=4), urothelial cancer (n=2), and ovarian cancer (n=1). Shifts were detected at all tested mononucleotide loci in all tumors. Amplification of BAT26 and BAT25 failed in one reaction from one endometrial carcinoma, respectively. Shift lengths for CASP2, BAT25, and BAT26 are listed in Table 2.

TABLE 2

|     | CAT25 | BAT25 | BAT26 |
|-----|-------|-------|-------|
| EC1 | 3     | 5     | na    |
| EC2 | 3     | 4     | 3     |
| EC3 | 8     | 3     | 6     |
| EC4 | 3     | na    | 5     |
| UC1 | 5     | 3     | 3     |
| UC2 | 4     | 2     | 3     |
| OC1 | 7     | 2     | 6     |

Shift lengths (nucleotides) observed in extracolonic MSI-H tumor lesions (EC—endometrial cancer, UC—urothelial cancer, OC—ovarian cancer)

Peak patterns of tumors EC3 and OC1 are presented in FIG. 5. FIG. 5 displays the distribution of CASP2, BAT25, and BAT26 product lengths in EC and OC samples. Products amplified from an MSI-H endometrial cancer (A) and an MSI-H ovarian cancer (B) are detailed in the Figure. PCR products are displayed for BAT26 (average relative product length 117 bp), BAT25 (109 bp), and CASP2 (147 bp). Filled peaks span the largest area and are defined as main product length. Shifts were observed exclusively in MSI-H tumours, shift lengths are denoted above the corresponding product peaks. Largest shift lengths are observed for CASP2. For details see Example 3.

EXAMPLE 4

Assessment Combination of CAT25 with Previously Published Quasimonomorphic Mononucleotide Markers in Patients from Caucasian Origin Combinations of CAT25 with other quasimonomorphic mononucleotide repeats were applied to test for MSI status of tumour samples. The quasimonomorphic mononucleotide repeats used for the present example were the following:

NR-21 (Suraweera et al. ("Evaluation of tumor microsatellite instability using five quasimonomorphic mononucleotide repeats and pentaplex PCR", Gastroenterology. 2002 December; 123(6):1804-11, Bacher et al. Development of a fluorescent multiplex assay for detection of MSI-High tumors. Dis Markers 2004; 20:237-50), NR-22 (Suraweera et al. (see above));

NR-24 (Suraweera et al. Bacher et al. 2004 (see above)),

Mono27 (Bacher et al. 2004 (see above))

Sample Preparation and Microsatellite Analysis

Preparation of tumor tissue samples, DNA extraction, and microsatellite instability analysis were performed as described in Example 1. DNA samples are described in Example 1. The following oligonucleotide primers were used for amplification:

```
NR-21   fwd   5'-TAAATGTATGTCTCCCCTGG-3'
              (SEQ ID NO: 42)
        rev   5'-ATTCCTACTCCGCATTCACA-3'
              (SEQ ID NO: 43)
NR-22   fwd   5'-GAGGCTTGTCAAGGACATAA-3'
              (SEQ ID NO: 44)
        rev   5'-AATTCGGATGCCATCCAGTT-3'
              (SEQ ID NO: 45)
```

```
-continued
NR-24   fwd   5'-CCATTGCTGAATTTTACCTC-3'
              (SEQ ID NO: 46)
        rev   5'-ATTGTGCCATTGCATTCCAA-3'
              (SEQ ID NO: 47)
Mono27  fwd   5'-TTGCAGTGAGCTGAGATTGC-3'
              (SEQ ID NO: 48)
        rev   5'-GGTGGATCAAATTTCACTTGG-3'
              (SEQ ID NO: 49)
```

Combination of CAT25 with Mono27, NR-21, NR-22, and NR-24 were evaluated in 37 MSI-H colorectal cancer specimens. In the presence of corresponding normal tissue, Mono27, NR-21, NR-24, and CAT25 detected MSI-H in all evaluable specimens, whereas NR-22 failed to detect MSI in 1 (2.9%) (HD-15) of the analyzable samples. A short summary of the results is given in FIG. 6. In the absence of matched normal tissue, sensitivity of the markers was 100% for Mono27, NR-21, and CAT25, compared to 34 (97.1) of 35 and 30 (96.8%) of 31 MSI-H CRC specimens for NR-22 and NR-24, respectively. Consequently, combinations of CAT25 with either NR-21, NR-22, or NR-24 were indicative of MSI-H in all analyzed colon cancer lesions.

Figure 7A:
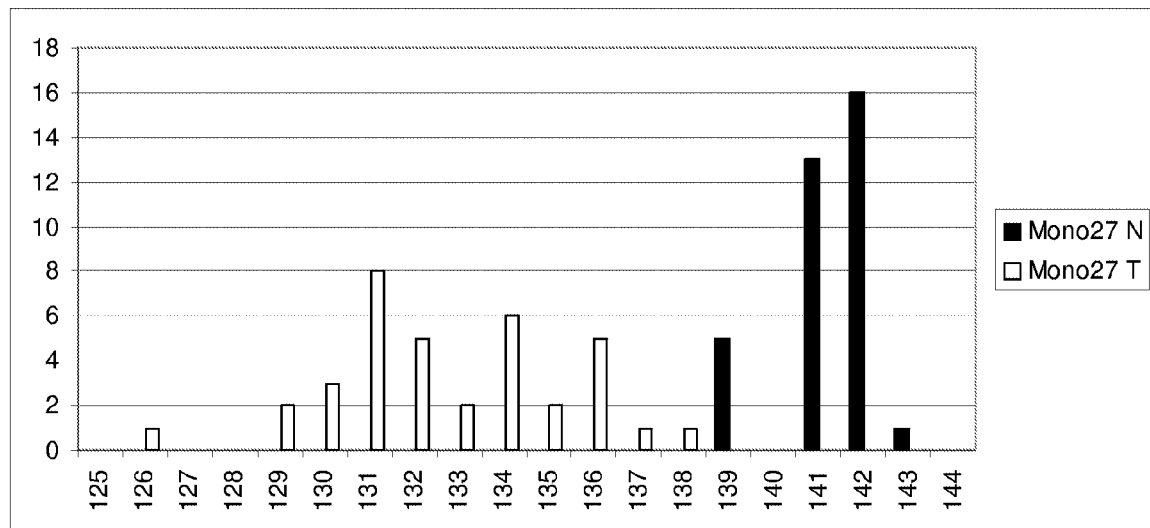
FIG. 7a: Allele length distribution of Mono27 in MSI-H CRC specimens (T, white columns) in comparison to normal non-tumorous tissue specimens (N, black columns). X axis represents relative allele length in base pairs, Y axis represents number of cases. For details compare Example 4.

Results of amplification are shown in FIGS. 7a to 7d. The Figures display graphically the allele length distribution of microsatellite markers Mono27, NR-21, NR-22, and NR-24 in MSI-H CRC specimens compared to normal non-tumorous tissue specimens. Whereas Mono27 and NR-21 clearly discriminated between MSI-H tumors and non-tumorous microsatellite stable tissues in all samples analyzed, overlaps were observed for NR-22 (white column 140 bp, FIG. 7c) and NR-24 (white column 129 bp, FIG. 7d). FIG. 7a displays allele length distribution of Mono27 in MSI-H CRC specimens (T, white columns) in comparison to normal non-tumorous tissue specimens (N, black columns). X axis represents relative allele length in base pairs, Y axis represents number of cases.

Figure 7B:
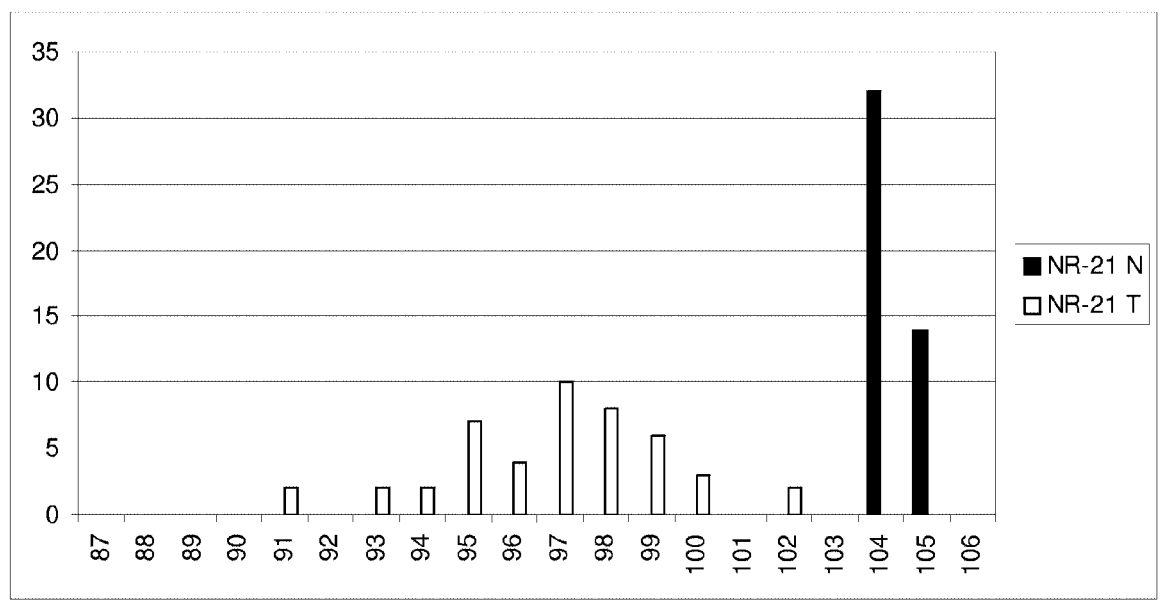
FIG. 7b: Allele length distribution of NR-21 in MSI-H CRC specimens (T, white columns) in comparison to normal non-tumororus tissue specimens (N, black columns). X axis represents relative allele length in base pairs, Y axis represents number of cases. For details compare Example 4.

FIG. 7b displays allele length distribution of NR-21 in MSI-H CRC specimens (T, white columns) in comparison to normal non-tumorous tissue specimens (N, black columns). X axis represents relative allele length in base pairs, Y axis represents number of cases.

Figure 7C:
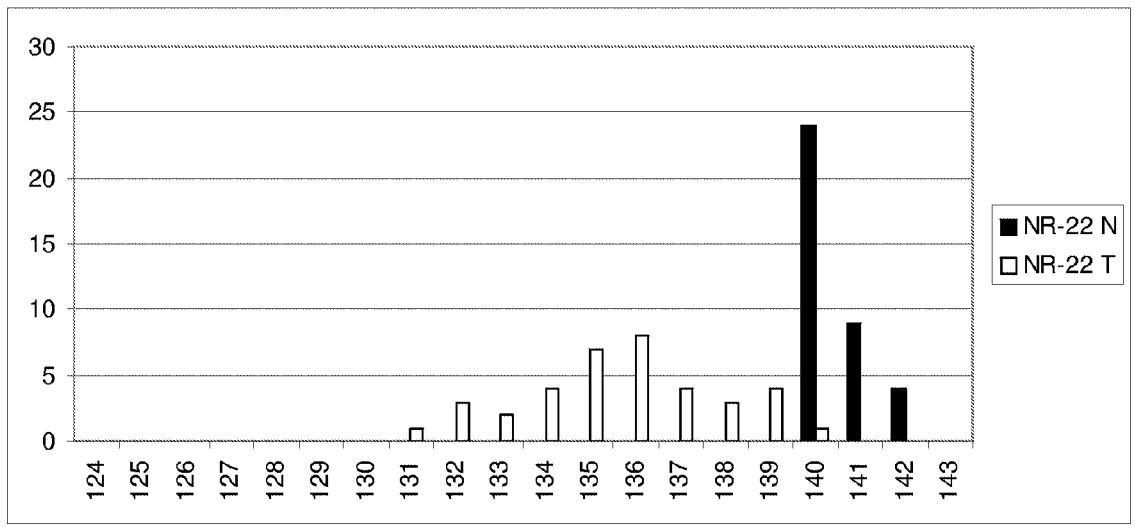
FIG. 7c: Allele length distribution of NR-22 in MSI-H CRC specimens (T, white columns) in comparison to normal non-tumororus tissue specimens (N, black columns). X axis represents relative allele length in base pairs, Y axis represents number of cases.

FIG. 7c displays allele length distribution of NR-22 in MSI-H CRC specimens (T, white columns) in comparison to normal non-tumorous tissue specimens (N, black columns). X axis represents relative allele length in base pairs, Y axis represents number of cases.

Figure 7D:
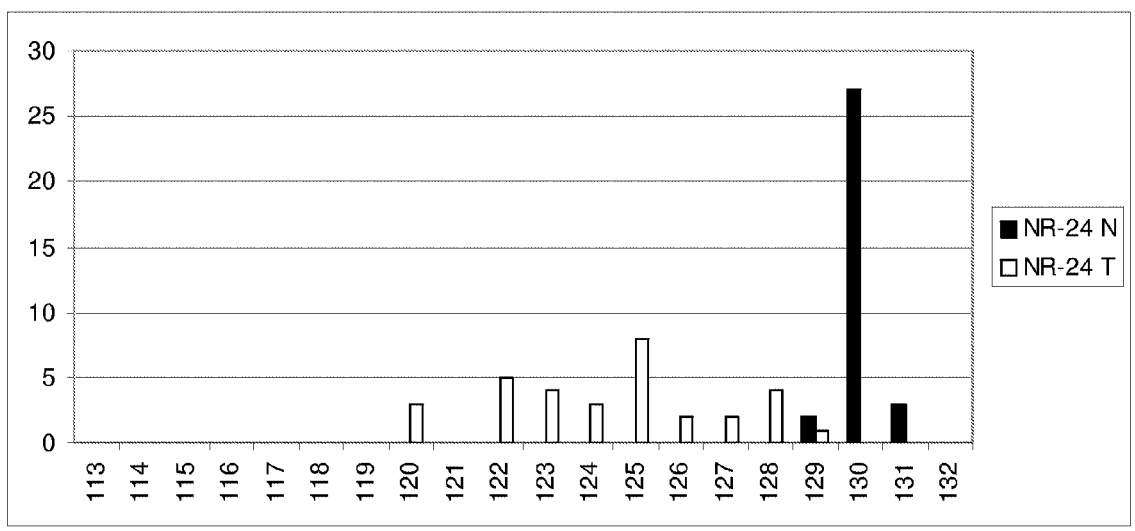
FIG. 7d: Allele length distribution of NR-24 in MSI-H CRC specimens (T, white columns) in comparison to normal non-tumorous tissue specimens (N, black columns). X axis represents relative allele length in base pairs, Y axis represents number of cases.

FIG. 7d displays the allele length distribution of NR-24 in MSI-H CRC specimens (T, white columns) in comparison to normal non-tumorous tissue specimens (N, black columns). X axis represents relative allele length in base pairs, Y axis represents number of cases.

Mean Basepair Deletion (bp)

| Mono27 | NR-21 | NR-22 | NR-24 | CAT25 |
|--------|-------|-------|-------|-------|
| 8.3    | 7.2   | 4.8   | 5.5   | 8.1   |
| 3.2    | 1.5   | 1.4   | 2.2   | 2.2   |

Largest mean basepair deletions (shift lengths) were observed for the markers Mono27 (8.3 bp) and CAT25 (8.1 bp). Markers NR-22 and NR-24 showed mean basepair deletions of 4.8 bp and 5.5 bp respectively. In summary, these data demonstrate that combination of CAT25 with NR-21, NR-22, NR-24, or Mono27 in duplex, triplex or multiplex amplification reactions represents a useful tool for the reliable detection of the MSI-H phenotype.

Allele Length Distribution of Mono27, NR-21, NR-22, NR-24 in Donors of African Origin In order to evaluate the allele length distribution of NR-21, NR-22, NR-24, and Mono27 in dependence of the donors' ethnic origin, these markers were amplified from normal tissue DNA obtained from donors of African origin who displayed the highest degree of heterozygosity in BAT25 and BAT26 compared to all other examined ethnic groups.

Figure 8A:
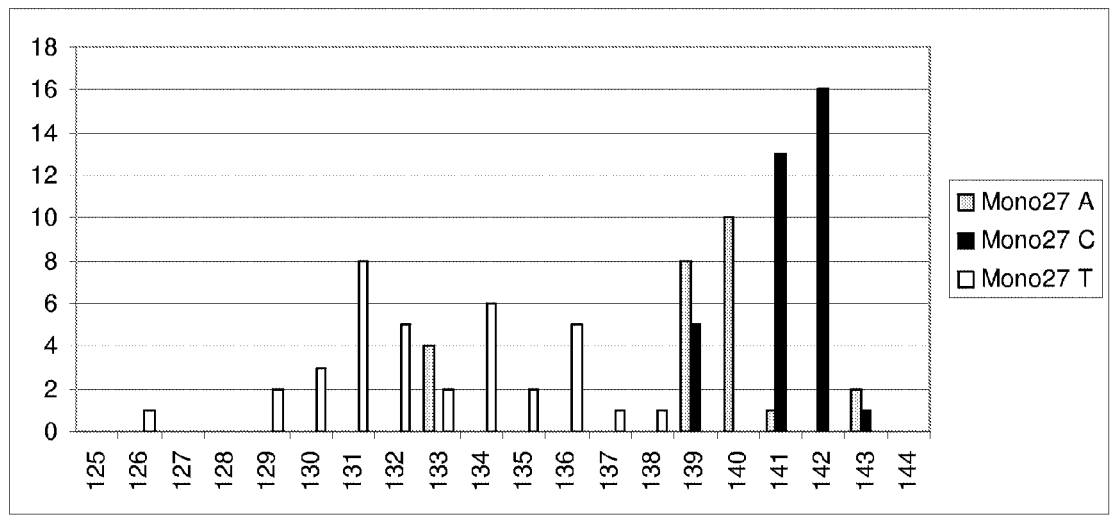
FIG. 8a: Allele length distribution of Mono27 in African donors The figure displays graphically the allele length distribution of microsatellite markers Mono-27 in MSI-H CRC specimens (T, white columns) in comparison to normal non-tumororus tissue specimens from Caucasian (C, black columns) and African donors (A, gray columns). X axis represents relative allele length in base pairs, Y axis represents number of cases. The figure displays the number of detected cases (y-axis) showing different relative allele lengths. For details refer to Example 4.
Figure 8B:
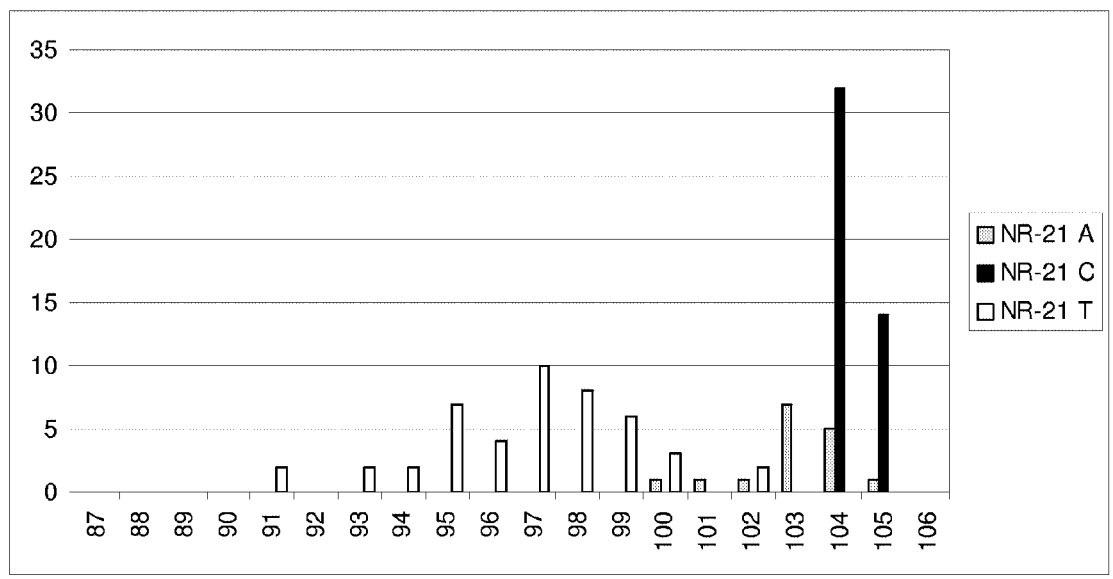
FIG. 8b: Allele length distribution of NR-21 in African donors The figure displays graphically the allele length distribution of microsatellite markers NR-21 in MSI-H CRC specimens (T, white columns) in comparison to normal non-tumororus tissue specimens from Caucasian (C, black columns) and African donors (A, gray columns). X axis represents relative allele length in base pairs, Y axis represents number of cases. The figure displays the number of detected cases (y-axis) showing different relative allele lengths. For details refer to Example 4.
Figure 8C:
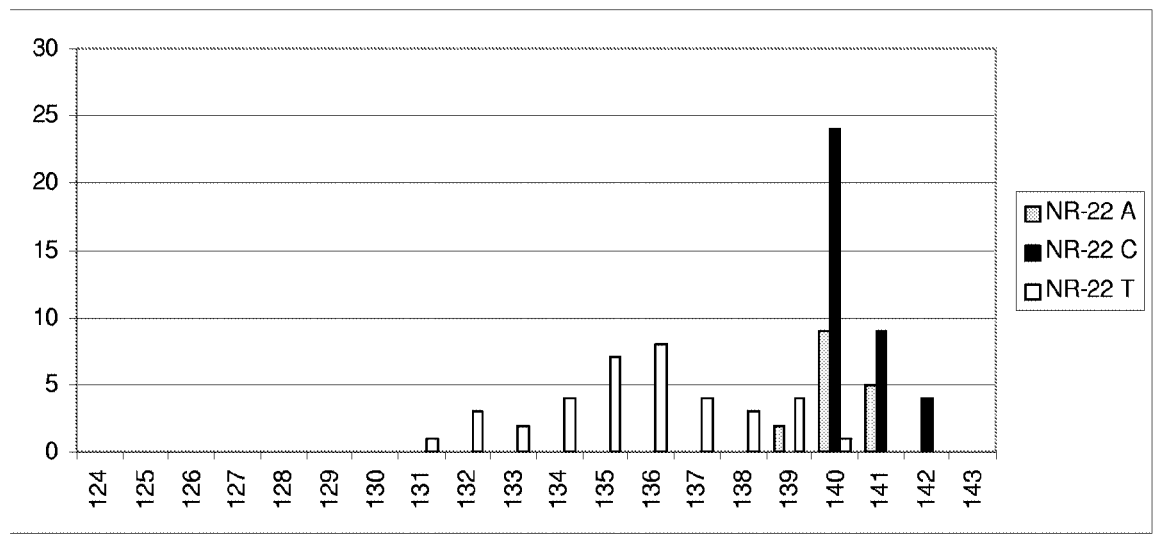
FIG. 8c: Allele length distribution NR-22 in African donors The figure displays graphically the allele length distribution of microsatellite markers NR-22 in MSI-H CRC specimens (T, white columns) in comparison to normal non-tumororus tissue specimens from Caucasian (C, black columns) and African donors (A, gray columns). X axis represents relative allele length in base pairs, Y axis represents number of cases. The figure displays the number of detected cases (y-axis) showing different relative allele lengths. For details refer to Example 4.
Figure 8D:
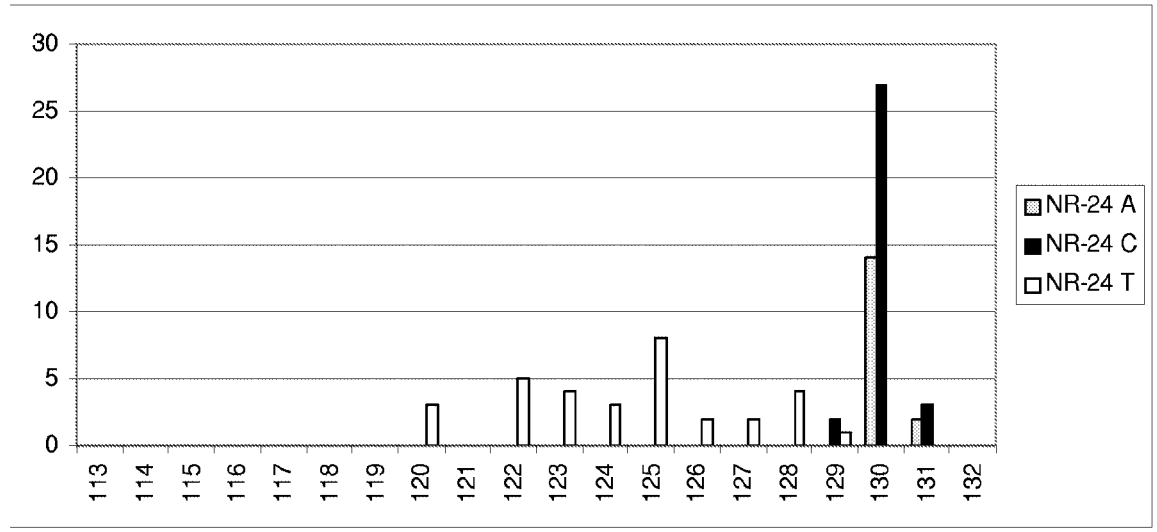
FIG. 8d: Allele length distribution of NR-24 in African donors The figure displays graphically the allele length distribution of microsatellite markers NR-24 in MSI-H CRC specimens (T, white columns) in comparison to normal non-tumororus tissue specimens from Caucasian (C, black columns) and African donors (A, gray columns). X axis represents relative allele length in base pairs, Y axis represents number of cases. The figure displays the number of detected cases (y-axis) showing different relative allele lengths. For details refer to Example 4.

Analysis of allele length distribution revealed a quasi-monomorphic pattern for NR-24 (FIG. 8d), whereas allele size variations>1 bp were detected for the markers Mono27 (see FIG. 8a) in 4 (16%) of 25, for NR-21 (see FIG. 8b) in 3 (18.8%) of 16, and for NR-22 (see FIG. 8c) in 2 (12.5%) of 16 individuals of African origin.

FIG. 8a to 8d display graphically the allele length distribution of microsatellite markers Mono27, NR-21, NR-22, and NR-24 in MSI-H CRC specimens (T, white columns) in comparison to normal non-tumororus tissue specimens from Caucasian (C, black columns) and African donors (A, gray columns). X axis represents relative allele length in base pairs, Y axis represents number of cases.

These data demonstrate that allelic size variation in individuals of African origin is highest for Mono27, but also present for NR-21 and, to a lesser extent, for NR-22 in the tested individuals of African origin. Although the analysis of larger collectives of different ethnic origin will be necessary to define the allele length distribution of all these markers in different ethnic groups, these data suggest that NR-22 and NR-24 may be combined with CAT25 in multiplex amplification reactions to obtain maximal sensitivity and specificity for microsatellite analysis in a variety of ethnic groups including those of African origin.

EXAMPLE 5

Use of Polymorphic Markers for Verification of Sample Identity

Polymorphic markers may be included to verify sample identity. In particular, sample identity can thus be assured when amplifying DNA obtained from more than one tumor specimen of the same patient or comparing tumor and corresponding normal tissue DNA of the same patient. Ideally, polymorphic markers used for this purpose have a high degree of heterozygosity. Their suitability for sample identification is based on the fact that they display sequence stability within one individual, but differ in allele length between different individuals. This example presents combination of CAT25 with the polymorphic tetranucleotide marker D3S1358 in a duplex PCR.

Sample Preparation and Microsatellite Analysis

Preparation of tumor tissue samples, DNA extraction, and microsatellite instability analysis were performed as described in Example 1. DNA samples have been described in Example 1. For the amplification of polymorphic marker D3S1358 the following oligonucleotide primers were used: fwd 5'-ACTGCAGTCCAATCTGGGT-3' (SEQ ID NO: 50), rev 5'-ATGAAATCAACAGAGGCTTG-3'(SEQ ID NO: 51).

Figure 9:
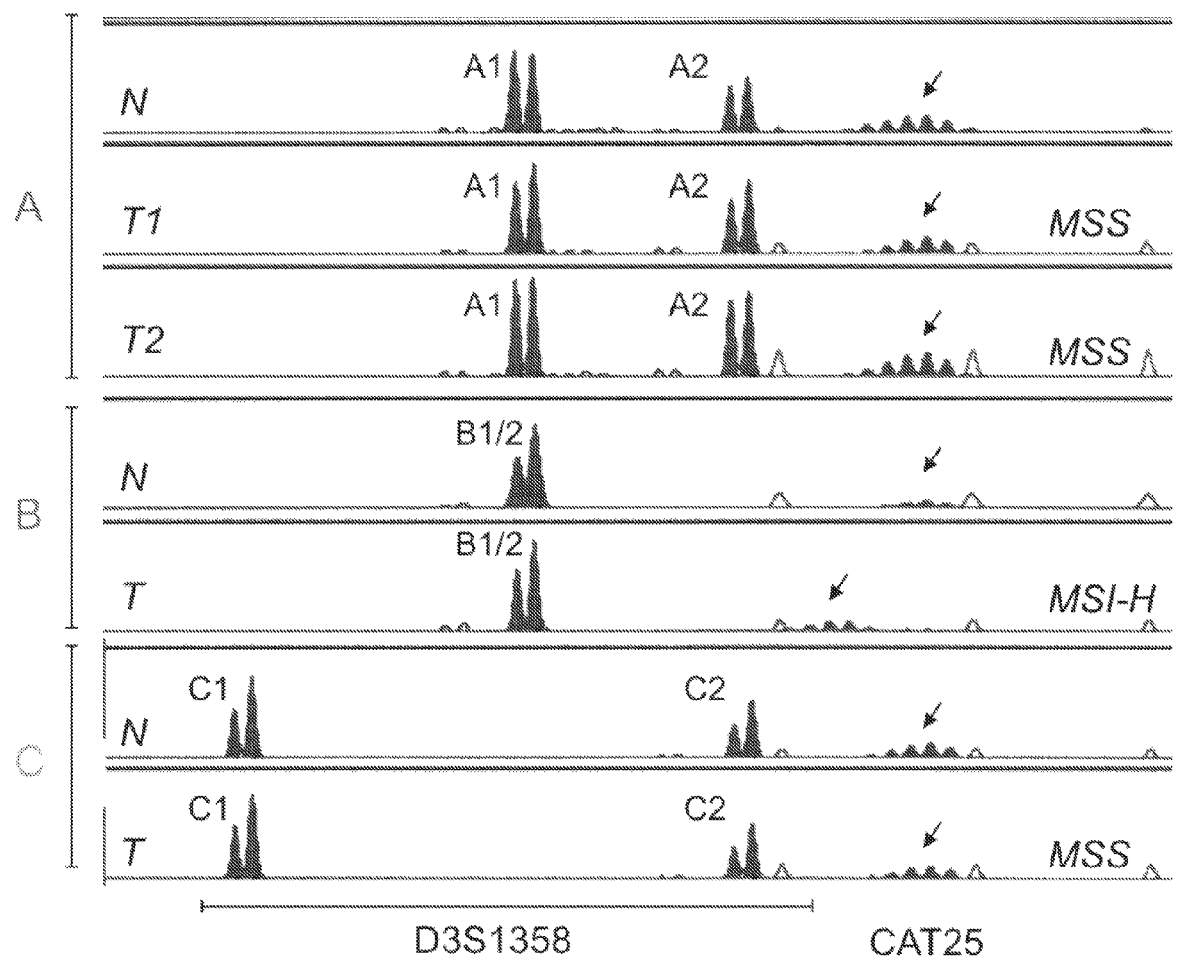
FIG. 9: Distribution of CAT25 and D3S1358 product lengths in three individuals for tumor and normal tissues. Relative product lengths observed for D3S1358 in normal and tumor tissue allows for unequivocal attribution of the normal tissue to the tumor tissue of one donor. This illustrates that polymorphic markers like D3S1358 may serve to allow matching of tumor and normal tissue of one donor. For details see Example 5.

Results are shown in FIG. 9. As can be seen from FIG. 9 the CAT25 alleles (arrows) are indicating microsatellite instability status of tumors (T) obtained from patients A, B, and C. Sample identification is assured by amplification of polymorphic typing marker D3S1358. D3S1358 alleles indicating sample origin are marked by A1/2, B1/2, and C1/2 for donors A, B, and C, respectively.

Tumor tissue specimens obtained from patients A, B, C were examined for CAT25 allele length to determine MSI status and, simultaneously, for D3S1358 allele lengths to assure sample identity (FIG. 9). D3S1358 alleles (A1/2, B1/2, and C1/2) allowed for unequivocal attribution of tumor samples to matched normal tissue controls in the three displayed samples, independently from the MSI status of the tumor. The comparably low frequency of instability at the D3S1358 locus in MSI-H tumors (e.g. no instability in MSI-H tumor of individual B) render this marker, akin to other highly polymorphic tetra- and pentanucleotides, useful for the described application of testing sample identity.

What is claimed is:

1. A method for detecting a high level microsatellite instability (MSI-H) phenotype in a human test tissue sample, comprising the steps:
   (a) obtaining a human test tissue sample, said test tissue sample comprising nucleic acids, wherein said test tissue sample is isolated from a tumor selected from the group consisting of tumors of the colorectal tract, colorectal carcinoma, colorectal adenoma, colorectal polyps, tumors of the gastrointestinal tract, carcinoma of the small intestine, polyps of the small intestine, endometrial tumors, endometrial carcinoma, endometrial hyperplasia, ovarian tumors, and urothelial tumors;
   (b) detecting the allele length of the CAT25 repeat in said nucleic acid; wherein the CAT25 repeat is the T25 (SEQ ID NO: 96) mononucleotide repeat, in exon 11 of the 3'-untranslated region of the Caspase 2 (CASP2) gene, amplifiable with a primer pair that is comprised of a first primer selected from the group consisting of SEQ ID NO: 1, 3, 5, 7, 9, 11, 13, 15, 17, 19 and 21, and a second primer selected from the group consisting of SEQ ID NO: 2, 4, 6, 8, 10, 12, 14, 16, 18, 20, and 22;
   (c) detecting the presence of a difference of the allele length of the CAT25 repeat in said human test tissue sample in comparison with the main allele lengths of the CAT25 repeat present in human control tissue samples that do not have an MSI-H phenotype; and
   (d) correlating the presence of a difference in the allele length of the CAT25 repeat with the presence of a MSI-H phenotype in said tissue.

2. The method of claim 1, wherein step (b) is carried out using a nucleic acid hybridization reaction or a nucleic acid amplification reaction.

3. The method of claim 1, wherein step (b) is carried out using nucleic acid probes or primers as binding agents.

4. The method of claim 3, wherein said test tissue is isolated from tumors of the colorectal tract, colorectal carcinoma, colorectal adenoma, or colorectal polyps.

5. The method of claim 3, wherein said test tissue is isolated from tumors of the gastrointestinal tract, carcinoma of the small intestine, or polyps of the small intestine.

6. The method of claim 3, wherein said test tissue is isolated from endometrial tumors, endometrial carcinoma, or endometrial hyperplasia.

7. The method of claim 3, wherein said test tissue is isolated from ovarian tumors or urothelial tumors.

8. The method of claim 1, wherein the probes or primers are selected from the group consisting of SEQ ID NOs: 1-22.

9. The method of claim 3, further comprising detecting one or more microsatellite markers other than the CAT25 repeat.

10. The method of claim 9, wherein the one or more microsatellite markers are selected from the group consisting of BAT25, BAT26, BAT40, APdelta3, NR-21, NR-22, NR-24 and Mono27.

11. The method according to claim 10, wherein the one or more microsatellite markers are BAT25 or BAT26.

* * * * *